United States Patent
Steichen et al.

(10) Patent No.: US 8,323,574 B2
(45) Date of Patent: Dec. 4, 2012

(54) METHOD AND APPARATUS FOR REDUCING A NITROGEN OXIDE, AND CONTROL THEREOF

(75) Inventors: John Carl Steichen, Landenberg, PA (US); Patricia A. Morris, Columbus, OH (US); John James Barnes, Hockessin, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 190 days.

(21) Appl. No.: 12/542,210

(22) Filed: Aug. 17, 2009

(65) Prior Publication Data

US 2009/0304559 A1 Dec. 10, 2009

Related U.S. Application Data

(62) Division of application No. 10/464,141, filed on Jun. 18, 2003, now Pat. No. 7,575,931.

(60) Provisional application No. 60/389,781, filed on Jun. 19, 2002.

(51) Int. Cl.
*G01N 27/00* (2006.01)
(52) U.S. Cl. ............... 422/83; 60/272; 60/274; 60/282; 60/286; 60/299; 60/301; 60/302; 60/303; 436/118; 422/62; 422/98
(58) Field of Classification Search .................. 436/118; 60/272, 274, 282, 286, 299, 301, 302, 303; 422/62, 83, 98
See application file for complete search history.

(56) References Cited

U.S. PATENT DOCUMENTS

| | | | |
|---|---|---|---|
| 4,007,435 A | 2/1977 | Tien et al. |
| 4,151,503 A | 4/1979 | Cermak et al. |
| 4,225,842 A | 9/1980 | Schlesselman et al. |
| 4,234,542 A | 11/1980 | Romine et al. |
| 4,347,732 A | 9/1982 | Leary |
| 4,387,359 A | 6/1983 | Tien et al. |
| 4,457,161 A | 7/1984 | Iwanaga et al. |
| 4,535,316 A | 8/1985 | Wertheimer et al. |
| 4,542,640 A | 9/1985 | Clifford et al. |
| 4,770,760 A | 9/1988 | Noda et al. |
| 4,963,332 A | 10/1990 | Brand |
| 5,047,220 A | 9/1991 | Polcer |
| 5,233,934 A | 8/1993 | Krigmont |
| 5,239,483 A | 8/1993 | Weir et al. |
| 5,426,934 A | 6/1995 | Hunt |
| 5,427,740 A | 6/1995 | Coles |
| 5,540,047 A | 7/1996 | Dahlheim et al. |
| 5,554,273 A | 9/1996 | Demmin et al. |
| 5,628,186 A | 5/1997 | Schmelz |

(Continued)

FOREIGN PATENT DOCUMENTS

EP 0293255 11/1988

(Continued)

OTHER PUBLICATIONS

Brent T. Marquis and John F. Vetelino, A semiconducting metal oxide sensor array for the detection of NOx and NH3, Sensors and Actuators B 77 (2001) 100-110.

(Continued)

*Primary Examiner* — Jill Warden
*Assistant Examiner* — Monique Cole

(57) ABSTRACT

Disclosed herein is a method and apparatus for reducing a nitrogen oxide, and the control thereof.

13 Claims, 9 Drawing Sheets

Sensor Array

U.S. PATENT DOCUMENTS

| | | | |
|---|---|---|---|
| 5,630,920 | A | 5/1997 | Friese et al. |
| 5,731,510 | A | 3/1998 | Jones et al. |
| 5,736,028 | A | 4/1998 | Hjortsberg et al. |
| 5,776,601 | A | 7/1998 | Foumier et al. |
| 5,832,411 | A | 11/1998 | Schatzmann et al. |
| 5,879,526 | A | 3/1999 | Dietz et al. |
| 5,952,555 | A | 9/1999 | Mobius |
| 6,012,282 | A | 1/2000 | Kato et al. |
| 6,082,176 | A | 7/2000 | Kondo et al. |
| 6,084,418 | A | 7/2000 | Takami et al. |
| 6,085,576 | A | 7/2000 | Sunshine et al. |
| 6,109,095 | A | 8/2000 | Addiego et al. |
| 6,170,318 | B1 | 1/2001 | Lewis |
| 6,235,243 | B1 | 5/2001 | Fleischer et al. |
| 6,849,239 | B2 | 2/2005 | Morris |
| 6,890,715 | B1 | 5/2005 | Lewis |
| 6,960,476 | B2 | 11/2005 | Morris |
| 7,065,958 | B2 * | 6/2006 | Funk et al. ............. 60/286 |
| 7,231,290 | B2 | 6/2007 | Steichen |
| 2002/0017467 | A1 | 2/2002 | Ando |
| 2004/0126286 | A1 | 7/2004 | DeRuyter |
| 2005/0063873 | A1 | 3/2005 | Morris |
| 2007/0202012 | A1 | 8/2007 | Steichen |

FOREIGN PATENT DOCUMENTS

| | | |
|---|---|---|
| EP | 0527258 | 2/1993 |
| EP | 0820799 | 1/1998 |
| JP | 04-176325 | 6/1992 |
| WO | WO93/08467 | 4/1993 |
| WO | WO00/00808 | 1/2000 |

OTHER PUBLICATIONS

G. Huyberechts, P. Szecowka, J. Roggen and B. W. Licznerski, Simultaneous quantification of carbon monoxide and methane in humid air using a sensor array and an artifical neural network, Sensors and Actuators B 45 (1997) 123-130.

Kazimierz Brudzewski and Stanishaw Osowski, Gas analysis system composed of a solid-state sensor array and hybrid neural network structure, Sensors and Actuators B 55 (1999) 38-46.

P. C. Jurs, G. A. Bakken and H. E. McClelland, Computational Methods for the Analysis of Chemical Senor Array Data from Volatile Analytes, Chem. Rev. 2000, 100, 2649-1678.

Keith J. Albert, Nathan S. Lewis, Caroline L. Schauer, Gregory A. Sotzing, Shannon E. Stitzel, Thomas P. Vaid and David R. Walt, Cross-Reactive Chemical Sensor Arrays, Chem. Rev. 2000, 100,1595-2626.

P. Vincenzini et al., Solid State Chemical and Biochemical Sensors, Advances in Science and Technology, 26, pp. 335-345, National Research Center, Italy, (1998).

PCT/US03/19443, International Search Report dated Oct. 16, 2003.

PCT/US01/32138, International Search Report dated Mar. 20, 2003.

S. W. Moore, J. W. Gardner and E. L. Hines, A modified multilayer perceptron model for gas mixture analysis, Sensors and Actuators B, 15-16 (1993) 344-348.

H. Meixner and U. Lampe, Metal oxide sensors, Sensors and Actuators B 33 (1996) 198-202.

J. Getino, J. Gutierrez, L. Ares, J. I. Robla, M. C. Horrillo, I. Sayago and J. A. Agapito, Intergrated sensor array for gas analysis in combustion atmospheres, Sensors and Actuators B 33 (1996).

Corrado Di Natale, Fabrizio Davide, Guido Faglia and Paolo Nelli, Study of the effect of the sensor operating temperature on SnO2-based sensor-array performance, Sensors and Actuators B 23 (1995) 187-191.

Antonio Pardo, Santiago Marco and Josep Samitier, Nonlinear Inverse Dynamic Models of Gas Sensing Systems Based on Chemical Sensor Arrays for Quantitative Measurments, IEEE Transactions on Instrumentation and Measurment, vol. 47, No, Jun. 1989, 644-651.

B. S. Hoffheins and R. J. Lauf, Performance of simplified chemical sensor arrays in a neural network-based analytical instrument, Analysis (1992) 20, 201-207, Elsevier, Paris.

Corrado Di Natale, Arnaldo D'Amico, Fabrizio A. M. Davide, Guido Faglia, Paolo Nelli and Giogio Sberveglieri, Performance evaluation of an SnO2-based sensor array for the quantitative measurement of mixtures of H2S and NO2, Senors and Actuators B, 20 (1994) 217-224.

H. Meixner, U. Lampe, J. Gerblinger and M. Fleischer, Chemosensors for motor management systems of the future, Fresenius J, Anal. Chem (1994) 348: 536-541.

* cited by examiner

Electrode Pattern

Dielectric Pattern

Sensor Material Pattern

METHOD AND APPARATUS FOR REDUCING A NITROGEN OXIDE, AND CONTROL THEREOF

This application is a division of and claims the benefit of U.S. application Ser. No. 10/464,141, filed Jun. 18, 2003, now U.S. Pat. No. 7,575,931, which by this reference is incorporated in its entirety as a part hereof for all purposes.

This application claims the benefit of U.S. Provisional Application No. 60/389,781, filed on Jun. 19, 2002, which is incorporated in its entirety as a part hereof for all purposes.

FIELD OF THE INVENTION

This invention relates to methods and apparatus for reducing a nitrogen oxide. In particular, it relates to the use of a gas analyzer to obtain information related to the compositional content of a multi-component gas mixture that contains a nitrogen oxide for the purpose of assisting in the control of the reduction.

TECHNICAL BACKGROUND

Oxides of nitrogen ($NO_X$) that are emitted by an emissions source, such as those formed as a result of combustion, are included among the main causes of the "acid rain" problem, the photochemical smog problem and the resulting damage to the environment. These harmful substances should therefore be eliminated to the greatest extent possible from the gases emitted by an emissions source, such as the exhaust from a combustion process, prior to their discharge into the atmosphere.

One source of nitrogen oxides, in the form of $NO_2$ and mainly NO, are those formed by the combustion of coal, oil, gas, gasoline, diesel fuel or other fossil fuels. Combustion of fossil fuels occurs, for example, in a stationary device such as furnace, which is a device for the production or application of heat. A furnace may be used in connection with a boiler such as in a steam generator that drives a steam turbine in an electrical generating plant, in connection with an industrial operation such as in a smelter or chemical reactor, or in connection with supplying heat for human consumption.

Fossil fuels are also combusted in a mobile device, including a device that supplies mechanical power such as an internal combustion engine in a vehicle for transportation or recreation, or in a piece of equipment for construction, maintenance or industrial operations; or in a gas turbine, which is a turbine driven by a compressed, combusted fluid (such as air), such as in the engine of a jet aircraft. Gas-emitting devices such as an internal combustion engine or a gas turbine are also found in stationary applications, however. The exhaust gas emitted by devices such as those described above is a multi-component mixture of gases containing nitrogen oxides. Nitrogen oxides are also emitted by plants for the incineration of industrial or municipal waste. In addition, carbon monoxide and hydrocarbons are also emitted by these sources.

A problem exists with respect to the need for control of the injection of a reducing agent into a gas mixture containing nitrogen oxides. There is a desire to effect the reduction of as large a quantity of the nitrogen oxides present in the gas mixture as possible. For this purpose, what amounts to a stoichiometric excess of reducing agent, in terms of the quantity of nitrogen oxides present, is often injected into the gas mixture and thus into the nitrogen oxides. An excess of reducing agent is employed not so much by design but primarily because of the unavailability of information related to the compositional content of the gas mixture sufficient to accurately calculate the stoichiometric equivalent of reducing agent needed. The compositional content of a gas mixture containing nitrogen oxides often varies in an extremely unpredictable manner as it moves through a conduit from its emission source to the point of its ultimate destination, such as a point of discharge into the atmosphere. As a result, because of the desire to obtain reduction of a large percentage of the nitrogen oxides, an amount of reducing agent is injected that later proves to be an excess. Whether this results from calculations based on inaccurate or incomplete information, a strategy of employing an excess to be certain that too little is not employed, or incomplete reaction of whatever the amount, the same undesired consequence is experienced—unreacted reducing agent is discharged to the atmosphere and becomes a pollutant itself. When ammonia is the reducing agent, this is known as ammonia slip. In a gas mixture that is unscrubbed, or otherwise contains sulfur oxides, unreacted ammonia is also capable of reacting with the sulfur oxides to yield corrosive, sticky deposits of ammonium sulfate and/or ammonium hydrogen sulfate that foul the mechanism of the conduit.

There is a need then for a method and apparatus for the reduction of a nitrogen oxide that provides control of the reaction of reduction, and in particular control of the injection of a reducing agent into the gas mixture containing the nitrogen oxide. In particular, there is a need for a method and apparatus that enables the calculation of the amount of reducing agent to be injected in relation to information about the compositional content of the gas mixture.

This invention addresses those needs by providing a method and apparatus in which analysis of the gas mixture is performed to furnish information related to the compositional content thereof. In certain embodiments, the analysis is furnished by a gas analyzer that may be placed within a conduit through which the gas mixture is transported in positions that create an opportunity to develop useful information about the gas mixture, and especially information related to the nitrogen oxide content thereof. In certain other embodiments, a gas analyzer is employed for this purpose that outputs a signal related to the content within the gas mixture of an individual component gas therein and/or the collective content of a sub-group of gases therein. In certain other embodiments, the information is inputted into a decision making routine and/or a map, and may be used to calculate a desired amount of reducing agent to be injected into the gas mixture, and thus into the nitrogen oxides to be reduced. Other embodiments of the invention are as more particularly described below, or are as would be apparent to the artisan in view of the description below.

SUMMARY OF THE INVENTION

One embodiment of this invention is an apparatus for reducing a nitrogen oxide gas emitted by a emissions source that involves (a) an exhaust conduit for transporting the nitrogen oxide gas downstream from the emissions source, (b) an injector for injecting a reducing agent into the conduit, and (c) one or more gas analyzers located in the conduit upstream from the injector.

Another embodiment of this invention, in a multi-component gas mixture that is emitted by a emissions source and contains a nitrogen oxide, wherein a nitrogen oxide is reduced by injecting a reducing agent into the gas mixture, is a method of determining the amount of reducing agent to be injected, or of decreasing the amount or release of unreacted reducing agent, by determining information as to the compositional content of the gas mixture, and controlling the injection of the reducing agent in relation to the information as to the compositional content of the gas mixture.

Another embodiment of this invention, in a multi-component gas mixture that is emitted by a emissions source and contains a nitrogen oxide, wherein a nitrogen oxide is reduced by injecting a reducing agent into the gas mixture and contacting the gas mixture with a catalyst, is a method of determining the amount of reducing agent to be injected, or of decreasing the amount or release of unreacted reducing agent by determining information as to the compositional content of the gas mixture before the gas mixture contacts any catalyst, and controlling the injection of the reducing agent in relation to the information as to the compositional content of the gas mixture.

Another embodiment of this invention, in a multi-component gas mixture that is emitted by a emissions source and contains a nitrogen oxide, wherein a nitrogen oxide is reduced by injecting a reducing agent into the gas mixture and contacting the gas mixture with a catalyst, is a method of determining the amount of reducing agent to be injected, or of decreasing the amount or release of unreacted reducing agent by determining information as to the compositional content of the gas mixture after the gas mixture has contacted a catalyst, and controlling the injection of the reducing agent in relation to the information as to the compositional content of the gas mixture.

Another embodiment of this invention, in a multi-component gas mixture that is emitted by a emissions source and contains a nitrogen oxide, wherein a nitrogen oxide is reduced by injecting a reducing agent into the gas mixture and contacting the gas mixture with a catalyst, is a method of determining the amount of reducing agent to be injected, or of decreasing the amount or release of unreacted reducing agent, by determining information as to the compositional content of the gas mixture after the gas mixture has contacted all catalyst, and controlling the injection of the reducing agent in relation to the information as to the compositional content of the gas mixture.

DETAILED DESCRIPTION OF THE INVENTION

Nitrogen oxides may be reduced by contact with a reducing agent in the absence of a catalyst at a temperature of about 850 to about 1200° C., preferably about 900 to about 1100° C. This is usually referred to as selective non-catalytic reduction. The most common way of providing a temperature high enough to perform the reduction is to inject the reducing agent into the gas mixture that contains the nitrogen oxides in or near the source, such as a source of combustion, from which the nitrogen oxides are being emitted. The nitrogen oxides are predominantly transformed by the high temperature of the source of emissions to molecular nitrogen, which is nontoxic. Ammonia (e.g. anhydrous ammonia) is a reducing agent typically used, but urea is an alternative choice as a reducing agent. Three to four times as much reducing agent is required in a non-catalytic reduction, as compared to a catalytic reduction (described below), to achieve the same extent of reduction.

More common, then, is selective catalytic reduction, in which diminution of the nitrogen oxide emitted by an emissions source, such as a source of combustion, takes place through contact of the nitrogen oxide and the reducing agent with a catalyst. In order to ensure an optimal utilization of the needed reducing agent, selective catalytic reduction processes are preferred for the removal of nitrogen oxides from emissions sources such as a combustion exhaust because of the oxygen content in the exhaust gas. As a reducing agent, ammonia gas (e.g. anhydrous ammonia) has proven itself to be suitable because it reacts easily with oxides of nitrogen in the presence of an appropriate catalyst for the reaction, but only to a slight extent with the oxygen present in the gas. Urea is an alternative choice as a reducing agent.

For the selective reduction of the nitrogen oxides contained in combustion exhaust gases, for example, it is known to feed into the exhaust gas stream vaporous ammonia ($NH_3$) under pressure, or ammonia dissolved in water, without pressure, while an effort is made, by means of a mixing section with appropriate baffling within the adjoining conduit gas passages, to achieve a streamer-free distribution of ammonia and temperatures in the flow of exhaust gas. The gas mixture emitted from a furnace flue may contain, for example, 1-20 percent by volume $O_2$, 40 to 2000 ppm by volume nitrogen oxides, and 10 to 5000 ppm by volume $SO_2$ and $SO_3$. The catalytic reduction of the nitrogen oxides by use of ammonia as a reducing agent typically proceeds according to one or more of these reactions:

$$4NO + 4NH_3 + O_2 \rightarrow 4N_2 + 6H_2O \qquad \text{I}$$

$$2NO_2 + 4NH_3 + O_2 \rightarrow 3N_2 + 6H_2O \qquad \text{II}$$

$$6NO + 4NH_3 \rightarrow 5N_2 + 6H_2O \qquad \text{III}$$

$$6NO_2 + 8NH_3 \rightarrow 7N_2 + 12H_2O \qquad \text{IV}$$

$$NO + NO_2 + 2NH_3 \rightarrow 2N_2 + 3H_2O \qquad \text{V}$$

Figure 4:
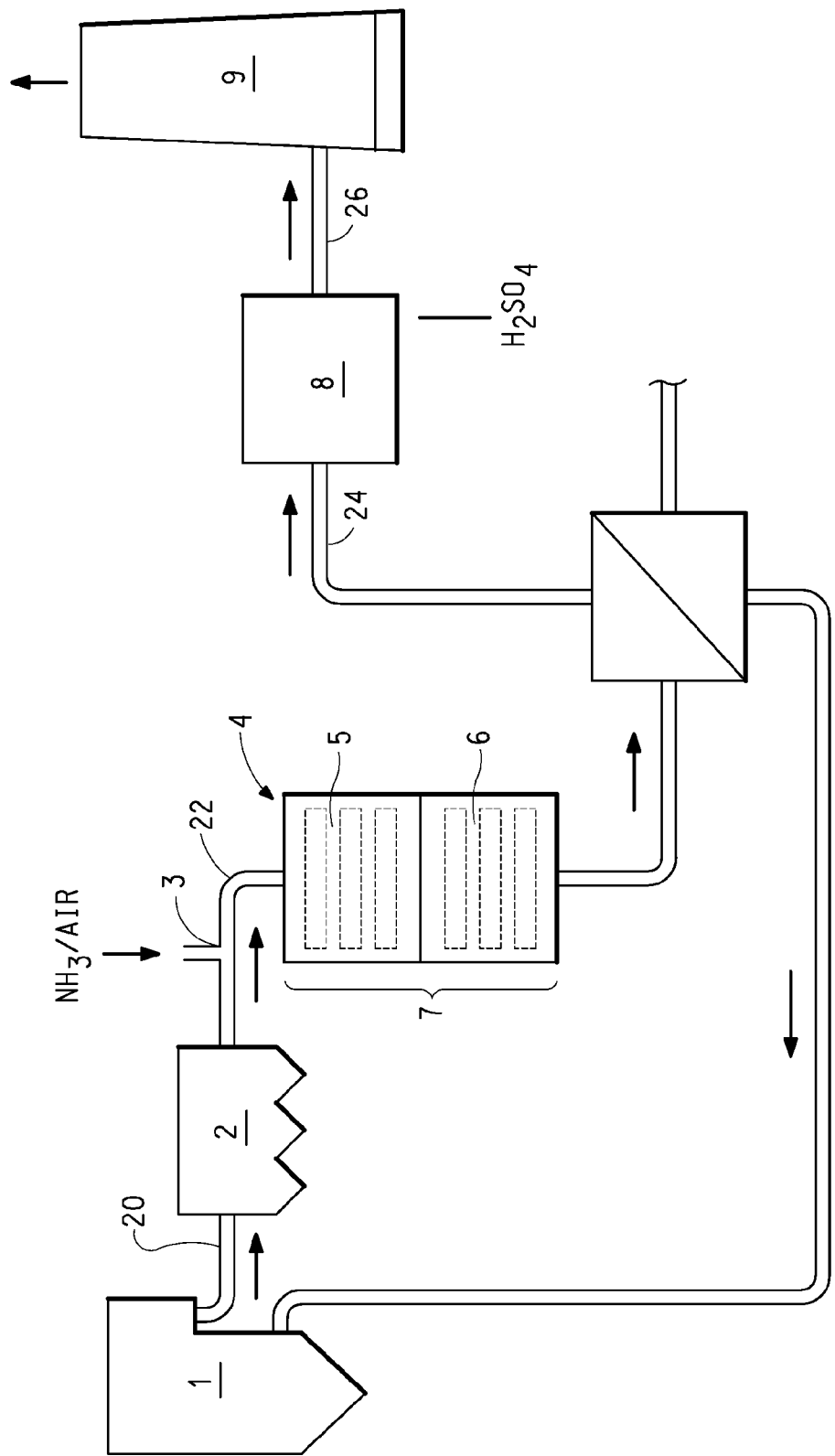
FIG. 4 is a schematic layout of the flow of a gas, such as the combustion exhaust from a boiler, through an SCR system.

As shown in FIG. 4, in a typical combustion process, flue gases emerging from a furnace (1) pass through a pipe (20) into a hot operating electrofilter (2) where they are freed of dust. An ammonia/air-mixture is then introduced into contact with the gases through injector (3), and is distributed homogeneously in the flow of the exhaust gas downstream from the filter (2). The mixture is then fed through pipe (22) into a catalytic reduction reactor (4).

It is shown in FIG. 4 that the catalyst (7) in the reactor (4) may be a vertical array of catalyst beds, a first series of beds (5) being positioned above a second series of beds (6). It is possible, if desired, to position a gas analyzer between individual catalyst beds, or between the first and second series of beds 5, 6. The catalyst may be in the form, for example, of monolithic, ceramic honeycomb catalysts disposed one behind the other to obtain the catalytic reduction of nitrogen oxide in the exhaust gas. There is a broad range for the permissible distances between the catalysts, or between the individual catalyst beds, located in the reactor (4). The dimensions of the spacing arrangement of the catalysts or catalyst beds are determined to insure the production of a turbulent transverse movement of gas in the conduit and avoidance of local mixing or "channeling".

From the reduction reactor (4), the gas mixture may, if desired, be transported through pipe 24 to a sulfur oxide scrubber (8) wherein sulfur oxide is reacted with water or dilute aqueous sulfuric acid to form concentrated $H_2SO_4$. The completely purified exhaust gas leaving the scrubber (8) may then be transported by pipe (26) to chimney (9) for discharge into the atmosphere. In FIG. 4, the exhaust is emitted from its source, the furnace (1), and is transported through piping and other components to its ultimate destination, the chimney (9), for discharge into the atmosphere. The direction of flow from the furnace (1) to the chimney (9) is considered to be downstream, and the opposite direction is considered to be upstream. The piping and other components through which the exhaust gas mixture is transported, and in which the reaction of reduction occur, together provide a conduit for the flow, transport, handling and disposition of the gas mixture. A gas analyzer, or the gas sensing component(s) thereof, can be positioned at any location along this conduit, whether in a pipe or within a component such as the catalyst (7) located in reactor 4. Multiple catalyst beds are illustrated in the apparatus of FIG. 4, and in similar fashion, the apparatus may contain a plurality of catalysts as well.

Figure 5:
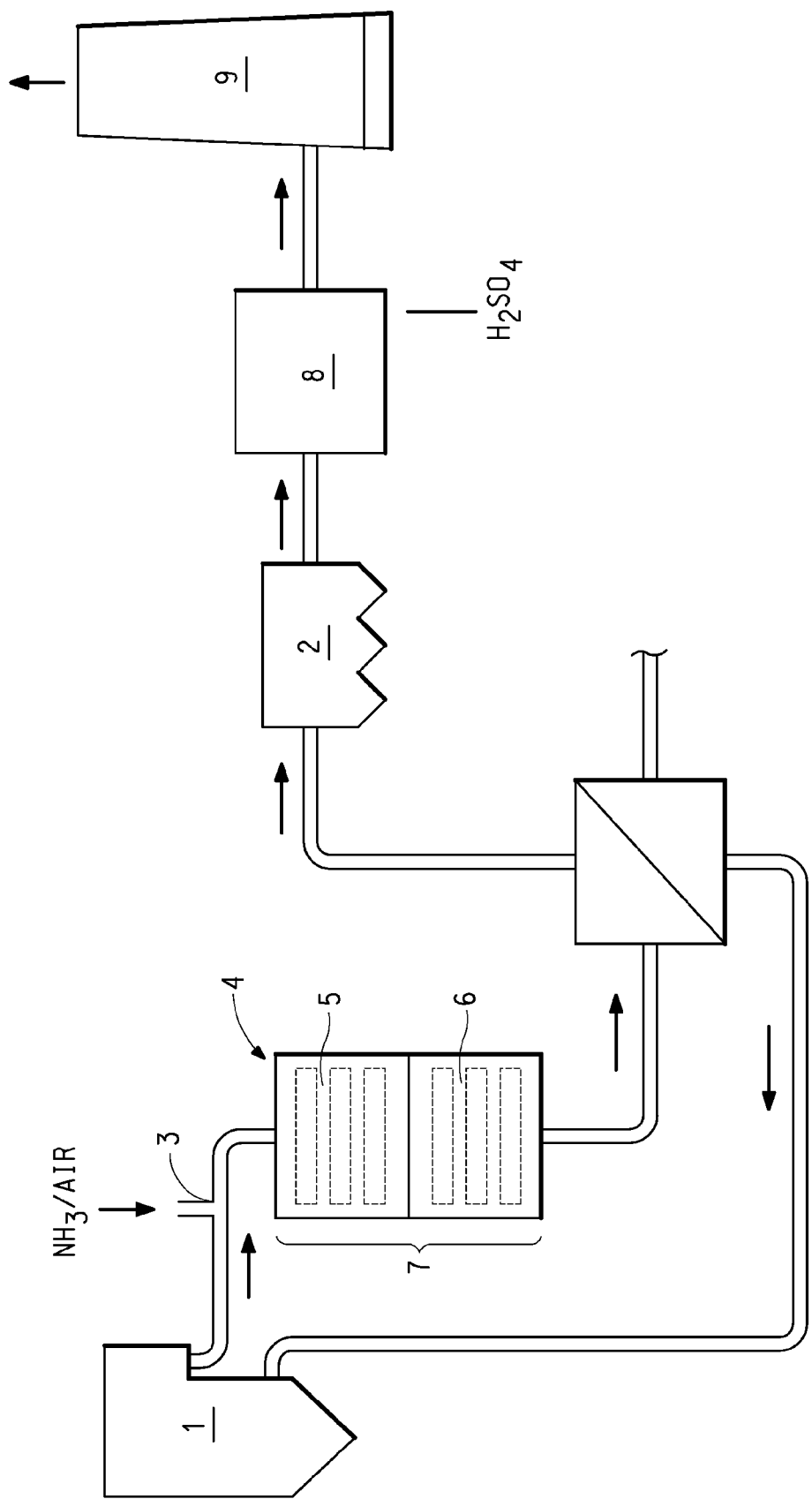
FIG. 5 is a schematic layout of the flow of a gas, such as the combustion exhaust from a boiler, through an SCR system.
Figure 6:
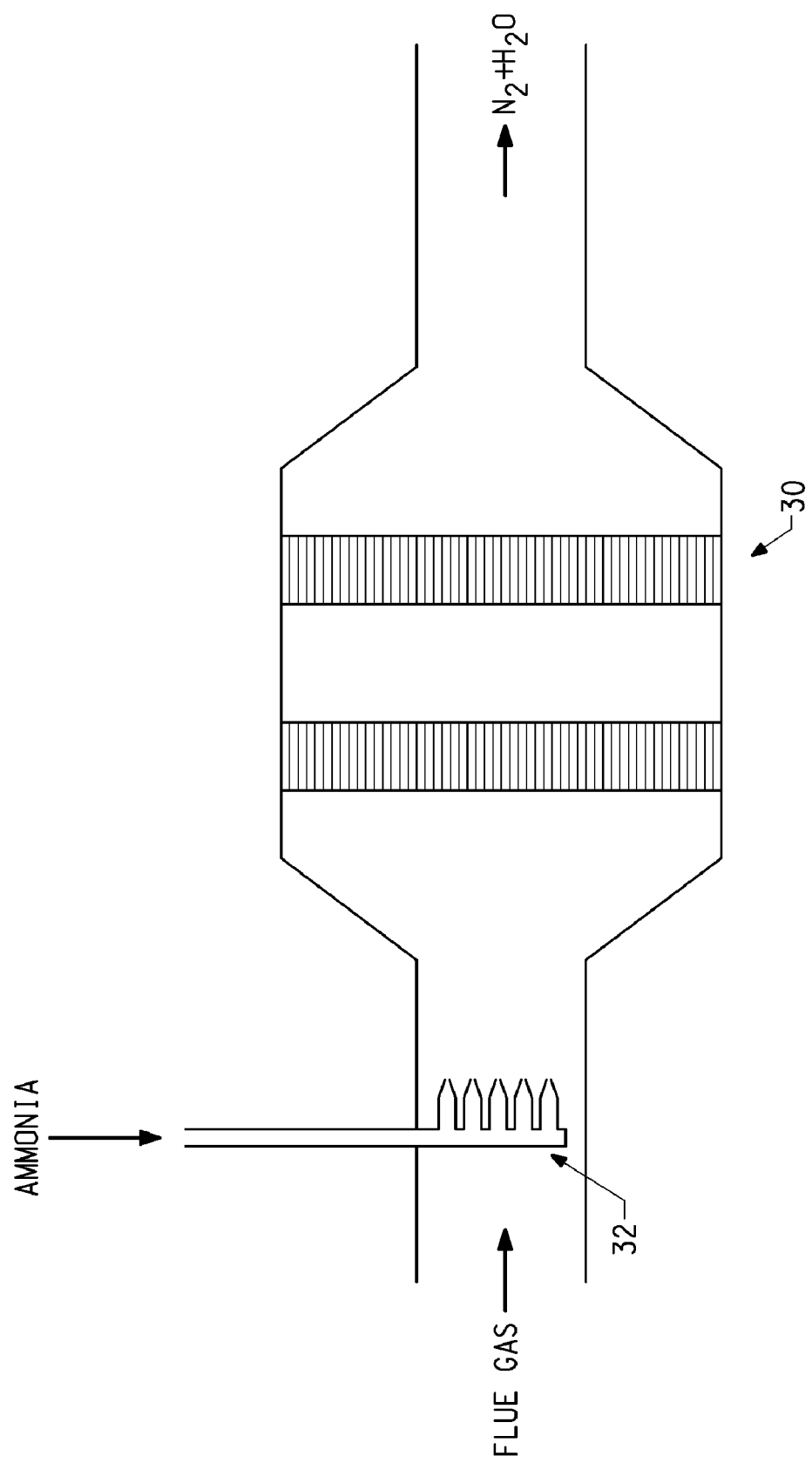
FIG. 6 shows the placement of a catalyst or a catalyst bed in an SCR system.

Alternatively, as shown in FIG. 5, a dust filter (2) may be located downstream from a catalyst (7). In a further alternative, as shown in FIG. 6, a gas mixture to be denitrified may pass horizontally through a reactor 30 containing one or more catalysts or catalyst beds. As described above, multiple catalysts and/or catalyst beds may be employed in this horizontal configuration, and one or more gas analyzers may be located between each of the catalysts and/or catalyst beds.

In the method according to the invention, essentially all catalysts may be used which are suitable for the selective reduction of nitrogen oxide. Examples of these are activated carbon, or catalysts that are mixtures of the oxides of iron, titanium (e.g. a manganese-based $TiO_2$), tungsten, vanadium and molybdenum (see, for example, DE 24 58 888, which is incorporated in its entirety as a part hereof for all purposes) or catalysts formed of natural or synthetic aluminum silicates, for example, zeolites (ZSM-5), or catalysts which contain precious metals of the platinum group. For example, a flue gas stream containing nitrogen oxides and sulphur oxides may be passed through a catalyst bed containing a catalyst consisting essentially of 3 to 15% by weight vanadium pentoxide ($V_2O_5$) on a carrier consisting of titanium dioxide ($TiO_2$), silica ($SiO_2$), and/or alumina ($Al_2O_3$).

The catalyst for nitrogen oxide reduction may be of any geometrical shape, such as in the form of a honeycomb monolith or in pellet or particulate form. However, a catalyst shape resulting in a large void and with parallel gas channels in the catalyst bed, such as a honeycomb catalyst, is preferred since the conduit gas often contains considerable amounts of dust which otherwise might clog the catalyst bed. The honeycomb form offers lower back pressure and a simpler possibility for cleaning off dust. A denitrification catalyst could be made for example as a carrier catalyst consisting of mullite honeycomb bodies of the dimensions 150 mm×150 mm×150 mm length with a cell density of $16/cm^2$ and a zeolite coating of the mordenite type. A moving bed is typically used for granular activated carbon.

The catalyst can consist completely of a catalytically active mass (solid catalyst), or the catalytically active substance can be deposited on an inert, ceramic or metallic body, which optionally can be coated in addition with a surface area enlarging oxide layer (carrier catalyst). For example, the catalyst may be in the form of a solid-bed reactor with a flow directed preferably vertically downward. The reactor may contain a honeycomb structure, which has a crystalline vanadium-titanium compound as the catalytically active substance. The pressure loss in the solid-bed reactor is taken into account in establishing the size of the conduit gas blower. The vertically downward flow in the reactor is intended to combat the depositing of solid impurities within the catalyst or keep them within acceptable ranges. The incrustation that occurs is removed discontinuously by blasting with compressed air or steam.

The catalytic reaction, preferably carried out in a single reactor, may be operated in the temperature range of about 250-550° C., preferably about 350-450° C., and more preferably about 380-420° C. The temperature should not be so high that the reducing agent is degraded (as in the conversion, for example, of ammonia into NOx and water), or so low that the reducing agent does not fully react with the emitted NOx, is released into the atmosphere and becomes a pollutant itself. The molar ratio of reducing agent to nitrogen oxides is typically in the range of about 0.6-1.8, and preferably about 1.0-1.4. In the case of a full load operation in a facility containing a combustion source such as an electrical generating plant, a flue gas temperature of 350-400° C. may be easily reached, and these are temperatures at which denitrification catalysts can be utilized. In the case of a variable load operation, the flue gas temperature drops as a rule below the minimum required for the operation of the catalyst in the partial load area, so that a bypass connection system is typically necessary for the branching off of flue gas before the last step of heat removal in the boiler in order to maintain the reaction temperature.

Operations that are carried out in the zone of high dust lead, moreover, to catalyst abrasion by the conduit dust, and may cause deposits and thus plugging up of the catalyst channels or pores. To prevent such complications, a cleaning by blowing off with (for example) hot steam is required at relatively short time intervals. It is preferred, however, that the reduction step be carried out using an exhaust gas which has little dust content or from which the dust has been largely removed because the mechanical and thermal load of the catalyst is considerably less. For the removal of the dust, the use of a high temperature electrofilter is particularly suitable. A filter of this type requires slightly higher investments in comparison to a cold operating electrofilter, but reheating measures and problems which are connected with the catalyst abrasion are avoided. Both embodiments in addition have the advantage that the removal dust is not contaminated with reducing agent.

To obtain an efficient decrease in the content of the nitrogen oxides in a flue gas, one approach as noted above, has been to add reducing agent in excess of the stoichiometric amount needed according to reactions I-V. If the reducing agent is not completely converted in the denitrification reaction, however, and a small quantity of it (designated as "ammonia slip" if the reducing agent is ammonia) is present in the exhaust gas after it is emitted into the atmosphere, the usual goal of limiting the content of reducing agent in treated flue gas to an acceptable level, such as 5-10 ppm by volume, will not be met. The alternative of utilizing less than stoichiometric amounts of reducing agent, and compensating by the use of increased volumes of catalyst, will increase the catalyst costs. The efficiency of the denitrification process will, moreover, be decreased as the absence of a stoichiometric amount of reducing agent will be the limiting factor in the reaction, and reduction of nitrogen oxides at an acceptable level will not occur. The methods and apparatus of this invention are used to furnish information about the compositional content of the gas mixture being subjected to denitrification to enable determination of the correct amount of reducing agent to be injected into the gas mixture, thereby decreasing the release of unreacted reducing agent.

For the purpose of controlling the denitrification reaction, it is also desirable to evaluate the success of the reaction by determining information about the compositional content of the gas mixture before it is emitted into the atmosphere. This type of determination may be made, for example, at one or more positions after the gas mixture has passed the point of injection of the reducing agent, if the reaction is uncatalyzed, or after the gas mixture has passed downstream from a reducing reactor if the reaction is catalyzed. Alternatively, if an oxidation catalyst is provided to oxidize unreacted reducing agent, the compositionally-related information may be determined at one or more positions after the gas mixture has passed downstream from the oxidation catalyst.

When such an oxidation catalyst is employed, and the reducing agent is for example, ammonia, ammonia is oxidized to nitrogen and water according to the following reaction:

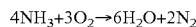
$$4NH_3+3O_2 \rightarrow 6H_2O+2N_2 \qquad \text{VI}$$

Typical oxidation catalysts for this purpose are based on transition metals, for example those containing oxides of copper, chromium, manganese and/or iron. A catalyst consisting essentially of about 2 to 7% by weight vanadium promoted with at least one alkali metal in a vanadium to alkali metal atomic ratio in the range from about 1:2 to 1:5 on a silica carrier is advantageously employed since this catalyst gives a high degree of conversion according to the reaction VI. The alkali metal employed is preferably potassium.

One example of the manner in which the methods and apparatus of this invention can be used to control the reduction of a nitrogen oxide is to control the injection of the reducing agent into the nitrogen oxide, such as by controlling the injection of the reducing agent into a gas mixture that contains a nitrogen oxide. In the case of nitrogen oxide that is emitted by a source of combustion, control of the reduction reaction may be effected in terms of the compositional content of the stream of exhaust gas given off by the combustion. Information may be obtained that is related to the compositional content of the exhaust gas at points in time both before and after a reducing agent has been injected into the nitrogen oxide.

Information related to the compositional content of a gas mixture containing a nitrogen oxide may be obtained from a gas analyzer that is exposed to the gas mixture. This is most conveniently done by placing one or more gas analyzers in a conduit in which the mixture containing the nitrogen oxide is transported from its source of emission to its eventual destination, such as discharge into the atmosphere. In the case of exhaust gas emitted from a source of combustion, this represents a challenge because combustion exhaust gases reach high temperatures that will degrade the materials and instrumentation from which many analytical devices are made. A gas analyzer as used in this invention is one that is not degraded by, or does not malfunction as a result of exposure to, a gas or gas mixture having a temperature of about 300° C. or more. Preferably the analyzer is not degraded or does not malfunction at even higher temperatures such as about 400° C. or more, about 500° C. or more, about 600° C. or more, about 700° C. or more, about 800° C. or more, about 900° C. or more, or about 1000° C. or more. The gas analyzer used in this invention, including the reactive or gas sensing components thereof, may thus be positioned in a gas mixture having a temperature as described above, and may thus be located in the same conduit in which the reducing agent is injected to effect the reduction reaction. Although the analyzer as it is installed in the conduit is connected to conductors that transmit signal outputs of the analyzer elsewhere for further processing, the only contact between the analyzer and the nitrogen oxide to be reduced, or the gas mixture containing the nitrogen oxides occurs in the conduit in which the nitrogen oxides are transported from their source to their eventual destination. The analyzer is not operated by withdrawing gas from the conduit for analysis in a separate chamber that is outside of the conduit.

A gas analyzer that is exposed to a gas mixture containing a nitrogen oxide is used to provide information related to the compositional content of the gas mixture for the purpose of controlling the reduction reaction. The information is used, in particular to control the injection of the reducing agent into the nitrogen oxide, such as by controlling the injection of the reducing agent into the gas mixture containing the nitrogen oxide. Information as to the compositional content of the gas mixture obtained before the reducing agent has been injected, or before the gas mixture has contacted a catalyst (if a catalyst is used), may be used to assist in the calculation of a stoichiometrically correct amount of reducing agent. This "stoichiometrically correct" amount is an amount that is sufficient to react with all nitrogen oxides present in the mixture without providing an excess of reducing agent that will be transported downstream with the mixture as a pollutant itself. Information as to the compositional content of the gas mixture obtained after the reducing agent has been injected may be used to evaluate the accuracy of the calculation by which the stoichiometrically correct amount of reducing agent is determined. If it appears that the calculation is not accurate because the gas mixture downstream from the injector, and downstream from the catalyst if a catalyst is used, contains more nitrogen oxide than desired or more reducing agent than desired, adjustments can be made to the calculation in view of such information obtained downstream from the position of the reduction reaction.

Figure 7:
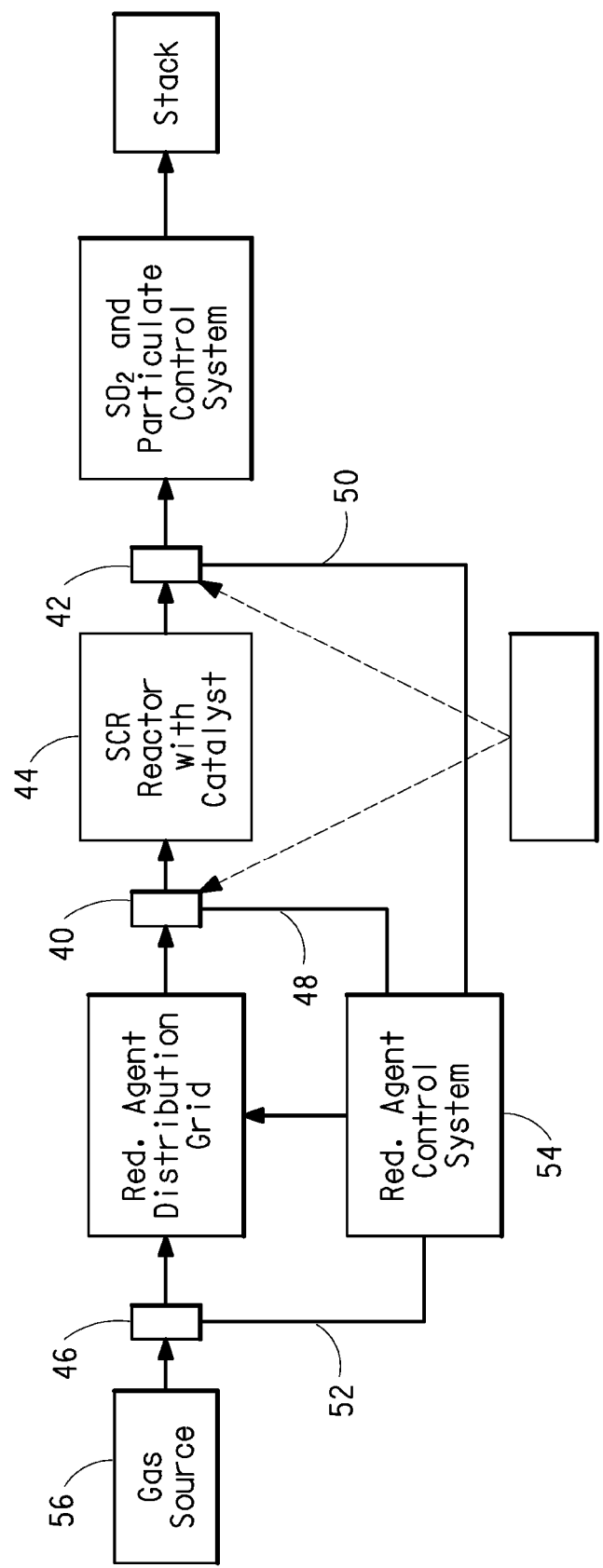
FIG. 7 is a schematic layout of the flow of a gas, such as the combustion exhaust from a boiler, through an SCR system containing a gas analyzer.

FIG. 7 shows a schematic layout of one possible placement of a gas analyzer both upstream 40 and downstream 42 from the position of a reduction reactor 44 in which a catalyst is employed, also upstream 46 from the point of injection of the reducing agent. By conductors 48, 50 and 52, information about the compositional content of the gas mixture is fed to a reducing agent control system 54. In addition to a pump for injecting the reducing agent, the reducing agent control system may contain a decision-making routine and/or a map. Information from gas analyzer 46 may be fed forward to control system 54 to assist in performing a first calculation of the amount of reducing agent to be injected into the gas mixture. Information from gas analyzer 40 may be fed back to control system 54 to evaluate whether the reducing agent is in place in the gas mixture to the extent and with the distribution as desired, and, in view of such finding, to also assist in performing adjustments as needed on the original calculation of the amount of reducing agent to be injected into the gas mixture. Information from gas analyzer 42 may be fed back to control system 54 to evaluate whether nitrogen oxide and the reducing agent are both absent from the gas mixture to the extent desired, and, in view of such finding, to also assist in performing adjustments as needed on the original calculation of the amount of reducing agent to be injected into the gas mixture.

The gas source 56 could be a stationary source of combustion, such as a furnace or a boiler for a steam turbine; a source of combustion that can be stationary, mobile or self-propelled such as a gas turbine or an internal combustion engine; or a chemical reaction that does not involve combustion such as an industrial process. Although ammonia is shown as the reducing agent, other reducing agents such as urea are also useful.

To control the operation of the reducing agent injector, the reducing agent control system performs certain decision-making routines about various operating characteristics of the reaction of reduction. The gas analyzers provide information to the control system about operating characteristics such as the amount and rate of injection of the reducing agent, about the presence of the reducing agent in the gas mixture before the reaction occurs, and about the success of the reaction in terms of the extent of presence of nitrogen oxide and/or reducing agent in the gas mixture after the reaction is completed. The reducing agent control system controls the injection of reducing agent by calculating an initial amount of reducing agent needed in view of the amount of nitrogen oxide determined to be present in the gas mixture, and by adjusting that calculation depending on the extent to which the reducing agent is successfully incorporated into the gas mixture before the reaction occurs, and depending on the extent to which nitrogen oxide has been reacted out of the gas mixture without reducing agent slip.

The decision-making routine in the reducing agent control system is run by a microprocessor chip, and applies one or more algorithms and/or mathematical operations to that information to obtain a decision in the form of a value that is equivalent to a desired state or condition that should be possessed by a particular operating characteristic. Based on the result of a decision-making routine, instructions are given by the reducing agent control system that cause a change in the rate or amount of injection of reducing agent thus moving the reduction reaction as close as possible to ideal performance, which is characterized by minimal residual nitrogen oxide and minimal reducing agent slip. In a preferred embodiment of this invention, a gas mixture that contains a nitrogen oxide that is reduced is, after the reduction reaction, free or substantially free of nitrogen oxide, and/or is free or substantially free of reducing agent.

In performing a decision-making routine, the reducing agent control system may, and preferably does, employ a map. A map resides in a read-only memory, and is an electronic collection of information about various operating characteristics of the reaction of reduction. In one embodiment, a range of quantified values may be set forth within the map with respect to a particular operating characteristic. This could be, for example, a range of temperature between 350 and 750° C., divided into 25° C. increments. With respect to each individual value of the parameter or operating characteristic in the range set forth, the map may then associate an acceptable value for one or more other operating characteristics, or a factor to be used in a decision-making routine. A map can be established in the form of a relational database, and can be accessed by look-up instructions in a computer program.

In the performance of a decision-making routine to control the operation of the reaction of reducing a nitrogen oxide, a value, such as the size of an electrical signal, that is representative of the state or condition of operating characteristic A may be inputted to the reducing agent control system. In one example of how the signal can then be utilized by a decision-making routine, the microprocessor chip determines a value representative of the state or condition each of operating characteristics B and C, and reads the map to determine, in view of the values for B and C, a target value D for operating characteristic A. The target value could be a preselected value that is recorded in the map as such, or could be a value that is calculated by the reducing agent control system by a mathematical operation recorded in the map, with the calculation to specify D being made only on the occasion when the values for B and C are determined. For example, a determination may be made of the absolute value of the difference between A and B, and this absolute value, when added to C, becomes the target value D.

The value of operating characteristic A is compared to target value D, and if A is in a desired relationship to D, the reducing agent control system does not instruct that any adjustment in operations be made. If A is not in a desired relationship to D, the decision-making process could, in further alternative embodiments, read the map to determine a desired value or range of values for A in terms of values for operating characteristics E and F; or calculate a desired value for A by reading the map to determine coefficients to be used in performing a mathematical operation on E and F. The values for E and F could be determined at the time of making the decision, or could be preselected values stored in the map. In either case, once the desired value for A is determined, the reducing agent control system instructs the necessary operating characteristics of the reaction of reduction to be adjusted in the manner necessary to obtain the desired value for A. This may be done by adjusting operating characteristic A itself, or adjusting other operating characteristics that can influence the state or condition of A. For example, the reaction of reduction may be controlled by adjusting the amount or frequency of injection of reducing agent, by adjusting the timing of injection by injectors in different locations, by heating or cooling the gas mixture or a reduction catalyst, and/or by adjusting the operation of the emissions source such as by adjusting the fuel to air ratio in a combustion reaction.

In this invention, information about the compositional content of the gas emitted by a chemical reaction, such as the exhaust gas of a source of combustion, may be used as an input to a decision-making in the reducing agent control system. In the example described above, information about combustion exhaust gas could be used as the representative value that is inputted with respect to any one or more of operating characteristics A, B, C, E or F, or could be used as a coefficient in a operation that the decision-making routine causes to be performed. Information about the gas composition is inputted to the decision-making routine, in this invention, in the form of one or more signals that is or are related to the individual concentration within the emitted gas stream of a particular individual component gas therein, or a particular subgroup of some but not all of the component gases therein, or both an individual component and a subgroup. The relationship may be a mathematical relationship, such as a monotonic relationship, involving for example a log, inverse or scaled value. This is accomplished by exposing a gas analyzer, such as an array of chemo/electro-active materials, to the emitted gas stream to generate that may be, for example, an electrical or optical signal.

The ability to furnish information about the individual concentration within an emitted gas stream of a particular component gas or subgroup therein makes it possible to calibrate a map. When building a map before a reaction or device to be controlled is put into service, values representative of a variety of parameters or operating characteristics must be determined by systematically operating the reaction or device under a large enough sample of different conditions to approximate all the conditions expected in actual service. A gas analyzer, such as an array of chemo/electro-active materials, can be used to analyze the composition of the emitted gas stream to furnish information based on the concentration of individual components or subgroups therein to be recorded in the map in relation to values of other parameters or operating characteristics measured under the same operating conditions.

If preferred, however, this ability to furnish information related to the concentration of individual components or subgroups in an emitted gas stream can be used to calibrate or re-calibrate a map in real time while the reduction reaction is in service. For example, a relationship could be established in a map between a value representative of the concentration of an individual gas component or subgroup, and values representative of various parameters or operating characteristics, with the value for the gas concentration to be supplied in real time. This might take the form of a decision-making routine involving a mathematical operation in which a value representative of the concentration of an individual gas component or subgroup is used as a factor or coefficient. The value representative of the concentration of an individual gas component or subgroup could remain undetermined until the time that the mathematical operation is performed in the execution of the decision-making routine to make the decision. The value representative of the concentration of an individual gas component or subgroup is determined and supplied to the decision-making routine only on the occasion of making the decision, and the decision thus need not be made based on information that may not be currently accurate at the time the decision is made. A map in which one or more parameters or operating characteristics is related to information about the concentration of an individual gas component or subgroup, with the information about the gas concentration being furnished in real time while a reaction or device is in service, clearly then has substantial value because it is possible to essentially recalibrate the map continually in real time.

In this invention, information about an emitted gas composition may be supplied to a map from a a gas analyzer employing one or more chemo/electro-active materials that furnishes an analysis of the emitted gas stream. Responses generated by the gas analyzer are then used as inputs, optionally along with the input from other sensors such as a temperature sensor, in the operation of algorithms that control the reaction of reduction.

In the case again of an engine, there are several ways in which a gas analyzer, such as an apparatus containing one or more chemo/electro-active materials, can be incorporated into the operation of a reducing agent control system to control the injection of reducing agent and to control, ultimately, the reaction of reduction. The chemo/electro-active materials may be constructed as an array of sensors that have sensitivity to individual gaseous components or subgroups of gases in a multi-component gas mixture, such as a stream of exhaust. Such sensors can be fabricated from semiconducting materials that respond uniquely to individual gases or gas subgroups that have common characteristics such as similar oxidation potential, electronegativity, or ability to form free radicals. These are properties of interest when characterizing combustion.

Typical examples of individual gases and subgroups of gases within an exhaust stream from a combustion reaction include oxygen, carbon monoxide, hydrogen, sulfur dioxide, ammonia, $CO_2$, $H_2S$, methanol, water, a hydrocarbon (such as $C_nH_{2n+2}$, and as same may be saturated or unsaturated, or be optionally substituted with hetero atoms; and cyclic and aromatic analogs thereof), a nitrogen oxide (such as NO, $NO_2$, $N_2O$ or $N_2O_4$) or an oxygenated carbon (CO, $CO_2$ or $C_5O_3$). The responses of an array of chemo/electro-active materials to the multi-component mixture of such gases formed by a stream of exhaust can thus be used to determine what type of control over a reaction of reduction is needed to execute a reaction in which nitrogen oxide content is decreased to the greatest extent possible without engendering unacceptable reducing agent slip.

Figure 8:
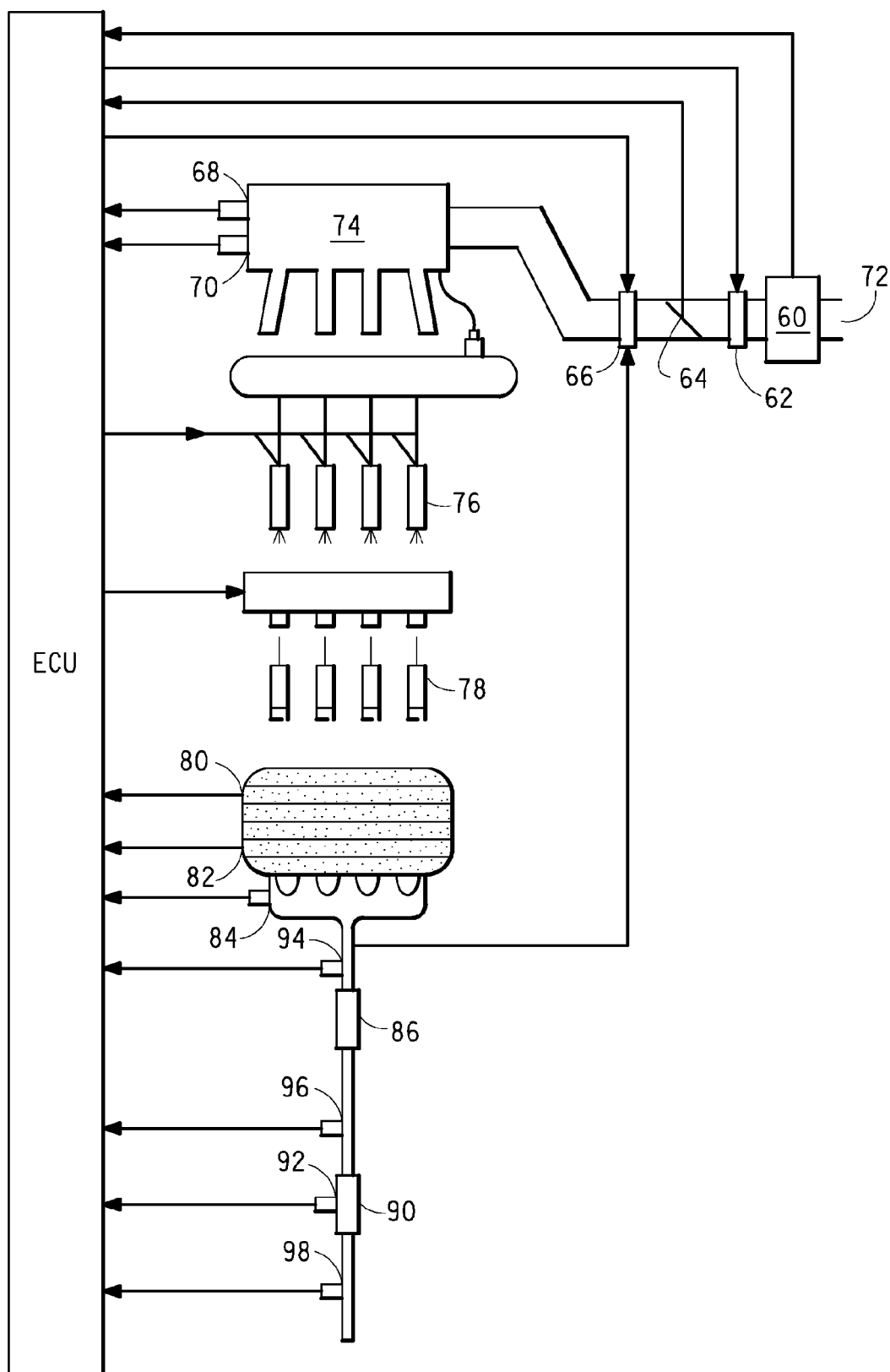
FIG. 8 is a schematic diagram of an internal combustion engine showing the placement of a gas analyzer.
Figure 9:
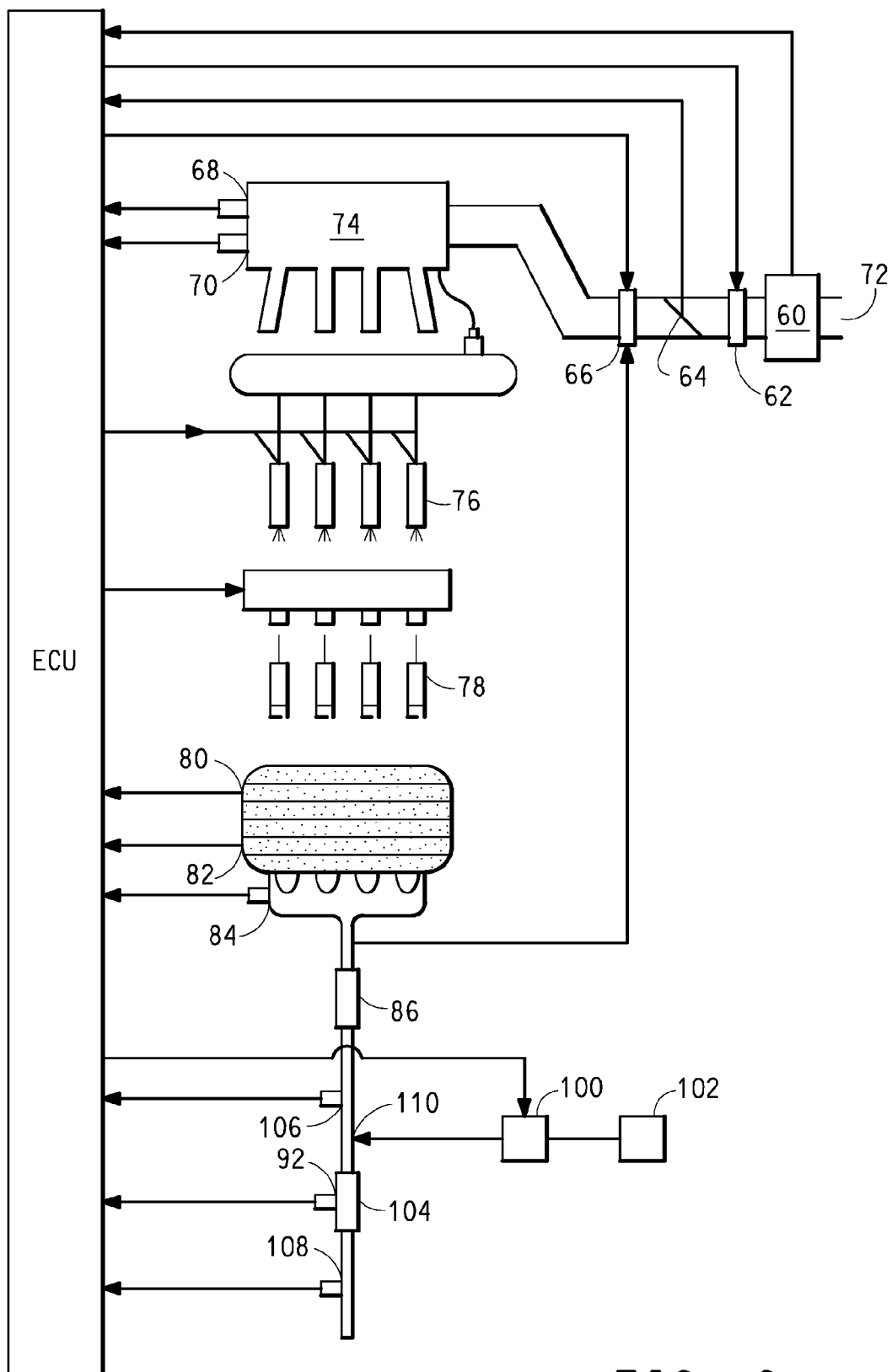
FIG. 9 is a schematic diagram of an internal combustion engine showing the placement of a gas analyzer in connection with an SCR system.

As an example, FIGS. 8 and 9 show several possible locations of a gas analyzer, such as an array of sensor materials, in the exhaust system of a vehicular internal combustion engine. The engine in FIGS. 8 and 9 contains a mass airflow and outside temperature sensor 60, an idle air valve 62, a throttle position valve 64, an exhaust gas recycle valve 66, an air temperature sensor 68, a pressure sensor 70, an air intake 72, an intake manifold 74, fuel injectors 76, spark plugs 78, a crank position sensor 80, a cam position sensor 82, a coolant temperature sensor 84, a pre-catalytic converter 86, an emissions control device (such as a catalytic converter and/or a device for the storage or abatement of NOx) 90, and a temperature sensor 92. The temperature sensor shown in FIGS. 8 and 9 need not be located adjacent the emissions control device 90 or the SCR catalyst 104, or additional temperature sensors may be located elsewhere along the exhaust conduit. FIG. 8 shows three possible locations 94, 96, 98 for a gas analyzer, which may be upstream or downstream from the emissions control device. The arrows indicate the locations where it would be possible, if desired, to provide for the flow of information to/from an engine control unit to/from one or more sensors or actuators.

A gas analyzer at position 94 is located close to engine and responds directly to the exhaust from individual cylinders. Because of its proximity and fast response, the array in this location can be used to obtain information from, or to control the operation of, each individual cylinder. An array in this location is exposed to very high exhaust temperatures for which semiconducting sensor materials are very suitable. A gas sensor in position 96 in FIG. 8 operates cooler and is exposed to gases that have already been modified in composition by the precatalyst. However, the gas stream at this point still contains much chemical information that can be used for control the reduction of nitrogen oxides. This is also a suitable location to employ feed-forward control by using an array of sensor materials to control operation of the catalytic converter, which catalyzes the completion of the oxidation of unburned fuel. Position 98 is a location that can be used to monitor engine emissions and the current state of the catalytic converter. Based on information from gas analyzer at this location, the catalytic converter can be regenerated or otherwise controlled through feedback process control.

FIG. 9 shows an SCR catalyst 104 and the deployment of gas sensors in a control system in which a reducing agent is injected into the exhaust conduit at position 110. Reducing agent is supplied from a reservoir 102 and is passed through reducing agent control system 100 for injection into the exhaust conduit. Reducing agent control system 100 includes the necessary pump to inject the reducing into the exhaust conduit, and is connected to the microprocessor chip for the passage of signals to and from the microprocessor chip to control the injection of reducing agent. A gas analyzer, such as a gas sensor, can in this arrangement be used either for feed-forward (position 106) or feedback (position 108) control. The gas sensor is responsive to a variety of gases that may be present in a combustion exhaust stream such as ammonia, nitrogen oxide, carbon monoxide, oxygen, hydrocarbons and water. The reducing agent control system, and the injection of reducing agent, may be controlled by information obtained from a gas analyzer that is positioned both upstream and/or downstream from a reduction catalyst and, optionally, upstream and/or downstream from the reducing agent injector. Information about the compositional content of the gas mixture containing a nitrogen oxide is provided to a decision-making routine and/or map in the microprocessor chip for processing into signals routed to the reducing agent pump, to the engine itself or to heating or cooling devices for the purpose of controlling the reaction of reduction.

An internal combustion engine, in which nitrogen oxide reduction is controlled by the methods and apparatus of this invention, can be used for many different purposes including, for example, in any type of vehicle for transportation or recreation such as a car, truck, bus, locomotive, aircraft, spacecraft, boat, jet ski, all-terrain vehicle or snowmobile; or in equipment for construction, maintenance or industrial operations such as pumps, lifts, hoists, cranes, generators, or equipment for demolition, earth moving, digging, drilling, mining or groundskeeping.

Although this invention has been described in detail with respect to the control of the reduction of nitrogen oxides generated by combustion, i.e. the oxidation of a fossil fuel, it is equally applicable to the reduction of nitrogen oxides that may be found in a gas mixture generated by any other type of chemical reaction. It is also equally applicable to the reduction of nitrogen oxides that are not in a mixture with other gases, where, for example, a gas analyzer is used to determine information related to the relative concentration within the group of nitrogen oxide of each individual nitrogen oxide. It is also equally applicable to reducing agents in addition to ammonia and urea.

It will thus be seen that, in various embodiments of this invention, as there may a plurality of reducing agent injectors, one or more gas analyzers may be located in the conduit upstream or downstream from each reducing agent injector. If a dust filter is used, it may be located upstream from a reducing agent injector and/or one or more gas analyzers.

If a catalyst is present, the catalyst may be located upstream or downstream from one or more gas analyzers. A first catalyst may be located upstream from one or more gas analyzers, and a second catalyst may be located downstream from one or more gas analyzers, particularly where the catalyst is a plurality of vertically arranged catalyst beds. A first gas analyzer may be located upstream from a catalyst, and a second gas analyzer may be located downstream from the catalyst. One or more gas analyzers may be located between first and second catalysts. One or more gas analyzers may be located at the point of destination of a flowing stream of a gas mixture, such as at a point of discharge to the atmosphere.

If a gas analyzer outputs a signal to a decision-making routine, a gas analyzer that is upstream from all catalyst, a gas analyzer that is downstream from a first catalyst and upstream from a second catalyst, and/or a gas analyzer that is downstream from all catalyst may each output a signal to a decision-making routine. A gas analyzer may output at least one signal that is related to the individual concentration within the gas mixture of an individual nitrogen oxide component therein, and/or may output at least one signal that is related to the collective concentration within the gas mixture of all nitrogen oxide components therein. The gas analyzer may in turn output a signal to a map. The gas analyzer may also output a signal to a decision-making routine that controls the injection of reducing agent, such as by calculating an amount of reducing agent to be injected.

Information as to the compositional content of a gas mixture may be determined before the injection of reducing agent, and/or before the gas mixture contacts any catalyst. Information as to the compositional content of a gas mixture may also be determined after the gas mixture contacts a first catalyst but before the gas mixture contacts a second catalyst, or after the gas mixture has contacted all catalyst. For example, a gas analyzer that is upstream from all catalyst, and a gas analyzer that is downstream from all catalyst may each output separate signals to a decision-making routine.

The injection of the reducing agent may be controlled in relation to such information as to the compositional content of the gas mixture, such as by determining the amount of reducing agent to be injected into the gas mixture. The information as to the compositional content of the gas mixture may be an output of one or more gas analyzers, and may be related to the individual concentration within the gas mixture of an individual gas component therein (such as a nitrogen oxide), and/or related to the collective concentration within the gas mixture of a subgroup of the component gases therein (such as all nitrogen oxides).

In the present invention, an array of chemo/electro-active materials is used for directly sensing one or more analyte gases in a multi-component gas system under variable temperature conditions. By "directly sensing" is meant that an array of gas-sensing materials will be exposed to a mixture of gases that constitutes a multi-component gas system, such as in a stream of flowing gases. The array may be situated within the gas mixture, and more particularly within the source of the gas mixture, if desired. Alternatively, although not preferred, the array may reside in a chamber to which the gas mixture is directed from its source at another location. When gas is directed to a chamber in which an array is located, the gas mixture may be inserted in and removed from the chamber by piping, conduits or any other suitable gas transmission equipment.

A response may be obtained upon exposure of the gas-sensing materials to the multi-component gas mixture, and the response will be a function of the concentrations of one or more of the analyte gases themselves in the gas mixture. The sensor materials will be exposed simultaneously (or substantially simultaneously) to each of the analyte gases, and an analyte gas does not have to be physically separated from the multi-component gas mixture to be able to conduct an analysis of the mixture and/or one or more analyte components thereof. This invention can be used, for example, to obtain responses to, and thus to detect and/or measure the concentrations, of combustion gases, such as oxygen, carbon monoxide, nitrogen oxides, hydrocarbons such as butane, $CO_2$, $H_2S$, sulfur dioxide, halogens, hydrogen, water vapor, an organo-phosphorus gas, and ammonia, at variable temperatures in gas mixtures such as automobile emissions.

Figure 1:
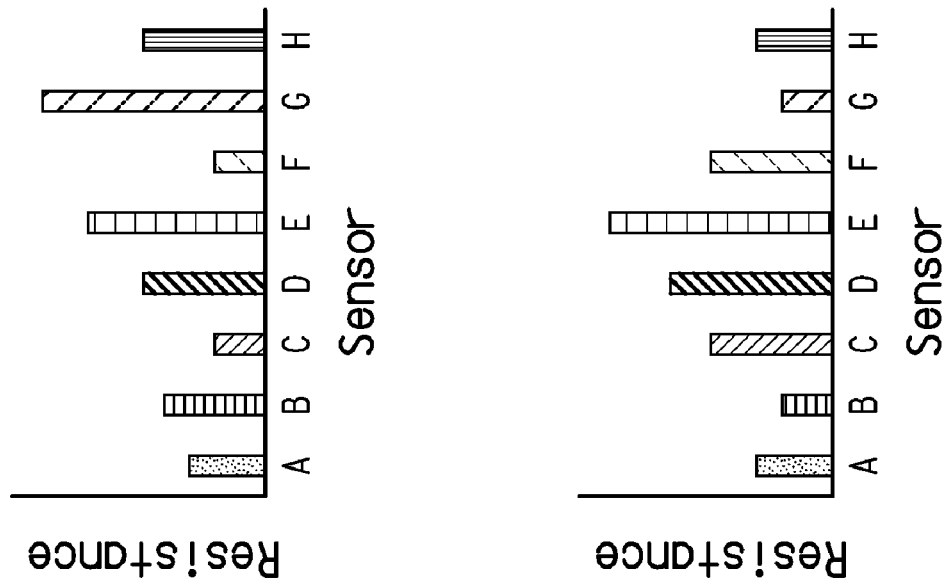
FIG. 1 depicts an array of chemo/electro-active materials.
Figure 1:
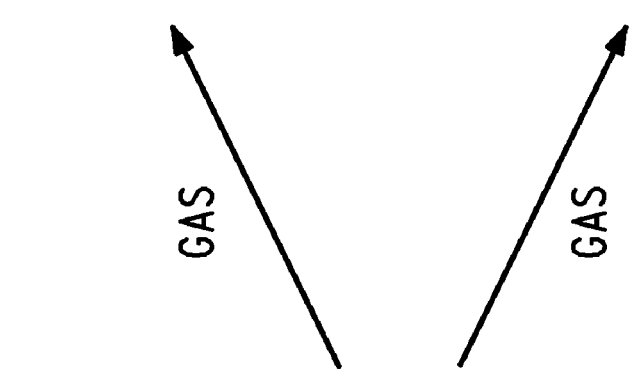
Figure 1:
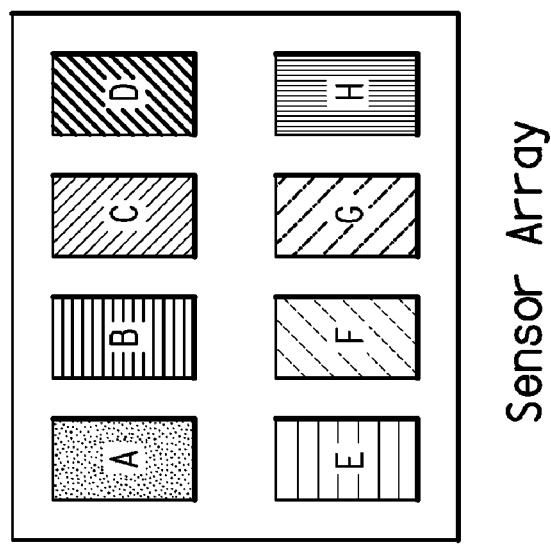

This invention utilizes an array of sensing materials to analyze a gas mixture and/or the components thereof to, for example, obtain a response to, detect the presence of and/or calculate the concentration of one or more individual analyte gas components in the system. By "array" is meant at least two different materials that are spatially separated, as shown for example in FIG. 1. The array may contain, for example, 3, 4, 5, 6, 8, 10 or 12 gas-sensing materials, or other greater or lesser numbers as desired. It is preferred that there be provided at least one sensor material for each of the individual gases or subgroups of gases in the mixture to be analyzed. It may be desirable, however, to provide more than one sensor material that is responsive to an individual gas component and/or a particular subgroup of gases in the mixture. For example, a group of at least 2, 3, 4, 5, 6, 7, 8, 9, 10, 11 or 12 sensors could be used to detect the presence of, and/or calculate the concentration of, one or more individual component gases and/or one or more subgroups of gases in the mixture. Groups of sensors, which may or may not have members in common, could be used to obtain a response to an analyte that is an individual gas component or a subgroup of gases in the mixture. A subgroup of gases that is, as the subgroup, an analyte may or may not contain as a member an individual gas that is itself also an analyte.

This invention is useful for detecting those gases that are expected to be present in a gas stream. For example, in a combustion process, gases that are expected to be present include oxygen, nitrogen oxides (such as NO, $NO_2$, $N_2O$ or $N_2O_4$), carbon monoxide, hydrocarbons (such as $C_nH_{2n+2}$, and as same may be saturated or unsaturated, or be optionally substituted with hetero atoms; and cyclic and aromatic analogs thereof), ammonia or hydrogen sulfide, sulfur dioxide, $CO_2$, or methanol. Other gases of interest may include alcohol vapors, solvent vapors, hydrogen, water vapor, and those deriving from saturated and unsaturated hydrocarbons, ethers, ketones, aldehydes, carbonyls, biomolecules and microorganisms. The component of a multi-component gas mixture that is an analyte of interest may be an individual gas such as carbon monoxide; may be a subgroup of some but not all of the gases contained in the mixture, such as the nitrogen oxides ($NO_x$) or hydrocarbons; or may be a combination of one or more individual gases and one or more subgroups. When a subgroup of gases is an analyte, a chemo/electro-active material will respond to the collective concentration within a multi-component gas mixture of the members of the subgroup together.

The analyte gas(es) contained in the mixture to which the chemo/electro-active material will be exposed can be a single gas, a subgroup of gases together, or one or more gases or subgroups mixed with an inert gas such as nitrogen. Particular gases of interest are donor and acceptor gases. These are gases that either donate electrons to the semiconducting material, such as carbon monoxide, $H_2S$ and hydrocarbons, or accept electrons from the semiconducting material, such as $O_2$, nitrogen oxides (commonly depicted as $NO_x$), and halogens. When exposed to a donor gas, an n-type semiconducting material will have a decrease in electrical resistance, increasing the current, and it, therefore, will show an increase in temperature due to $I^2R$ heating. When exposed to an acceptor gas, an n-type semiconducting material will have an increase in electrical resistance, decreasing the current, and therefore will show a decrease in temperature due to $I^2R$ heating. The opposite occurs in each instance with p-type semiconducting materials.

Obtaining information related to the compositional content of a gas mixture using these sensor materials, such as measurement of gas concentrations, can be based on a change in an electrical property, such as AC impedance, of at least one, but preferably each and all, of the materials upon exposure of the materials to a mixture containing one or more analyte gases. Analysis of a gas mixture can also be performed in terms of extent of change in other electrical properties of the sensor materials, such as capacitance, voltage, current or AC or DC resistance. Change in DC resistance may be determined, for example, by measuring change in temperature at constant voltage. The change in one of these illustrative properties of a sensor material is a function of the partial pressure of an analyte gas within the gas mixture, which in turn determines the concentration at which the molecules of the analyte gases become adsorbed on the surface of a sensor material, thus affecting the electrical response characteristics of that material. By using an array of chemo/electro-active materials, a pattern of the respective responses exhibited by the materials upon exposure to a mixture containing one or more analyte gases can be used to simultaneously and directly detect the presence of, and/or measure the concentration of, at least one gas in a multi-component gas system. The invention, in turn, can be used to determine the composition of the gas system. The concept is illustrated schematically in FIG. 1 and is exemplified below.

To illustrate, consider the theoretical example below of the exposure of a sensor material to a mixture containing an analyte gas. Where a response is obtained, the event is depicted as positive (+), and where no response is obtained, the event is depicted as negative (−). Material 1 responds to Gas 1 and Gas 2, but shows no response to Gas 3. Material 2 responds to Gas 1 and Gas 3, but shows no response to Gas 2, and Material 3 responds to Gas 2 and Gas 3, but shows no response to Gas 1.

|  | Material 1 | Material 2 | Material 3 |
| --- | --- | --- | --- |
| Gas 1 | + | + | − |
| Gas 2 | + | − | + |
| Gas 3 | − | + | + |

Therefore, if an array consisting of Materials 1, 2 and 3 gives the following response to an unknown gas,

|  | Material 1 | Material 2 | Material 3 |
| --- | --- | --- | --- |
| Unknown Gas | + | − | + | then the unknown gas would be identified as Gas 2. The response of each sensor material would be a function of the partial pressure within the mixture of, and thus the concentration of, an analyte gas or the collective concentration of a subgroup of analyte gases; and the response could be quantified or recorded as a processible value, such as a numerical value. In such case, the values of one or more responses can be used to generate quantitative information about the presence within the mixture of one or more analyte gases. In a multi-component gas system, chemometrics, neural networks or other pattern recognition techniques could be used to calculate the concentration of one or more analyte gases in the mixture of the system.

The sensing materials used are chemo/electro-active materials. A "chemo/electro-active material" is a material that has an electrical response to at least one individual gas in a mixture. Some metal oxide semiconducting materials, mixtures thereof, or mixtures of metal oxide semiconductors with other inorganic compounds are chemo/electro-active, and are particularly useful in this invention. Each of the various chemo/electro-active materials used herein preferably exhibits an electrically detectable response of a different kind and/or extent, upon exposure to the mixture and/or an analyte gas, than each of the other chemo/electro-active materials. As a result, an array of appropriately chosen chemo/electro-active materials can be used to analyze a multi-component gas mixture, such as by interacting with an analyte gas, sensing an analyte gas, or determining the presence and/or concentration of one or more analyte gases or subgroups in a mixture, despite the presence therein of interfering gases that are not of interest. Preferably the mole percentages of the major components of each gas-sensing material differs from that of each of the others.

The chemo/electro-active material can be of any type, but especially useful are semiconducting metal oxides such as $SnO_2$, $TiO_2$, $WO_3$ and ZnO. These particular materials are advantageous due to their chemical and thermal stability. The chemo/electro-active material can be a mixture of two or more semiconducting materials, or a mixture of a semiconducting material with an inorganic material, or combinations thereof. The semiconducting materials of interest can be deposited on a suitable solid substrate that is an insulator such as, but not limited to, alumina or silica and is stable under the conditions of the multi-component gas mixture. The array then takes the form of the sensor materials as deposited on the substrate. Other suitable sensor materials include single crystal or polycrystalline semiconductors of the bulk or thin film type, amorphous semiconducting materials, and semiconductor materials that are not composed of metal oxides.

In various embodiments, the substrate may be a high-temperature multilayer ceramic, which is prepared from $Al_2O_3$, AlN, and, to a smaller extent, BeO and SiC. The alumina content is dominant, however, with about 92-96 weight % of the composition being $Al_2O_3$. The structure consists of many layers of ceramic, with metallization between the layers, and via holes through the layers for electrical contact. A well known application of large modules with many layers of ceramic is IBM's pioneering product "Thermal Conduction Module" (TCM) for mainframe computers in 1983. The module had 33 layers, and 133 silicon chips were mounted by flip chip soldering.

This type of non-sintered, pliable ceramic consists of alumina powder, organic binders and solvents. The material is spread from a container down on a transport carrier underneath. The ceramic "tape" ("green sheet") is given the appropriate thickness on the transport carrier by passing underneath a "doctor blade" in a precisely controlled distance. The tape is cut to correct size, and holes and component cavities are punched out with a numerically controlled punching tool, or with a permanent, product specific punching tool for high production volume of a given product. Metallization of the via holes and fabrication of conductors is done by screen printing of tungsten (or molybdenum). These are the only metals that can withstand the high process temperature during the subsequent sintering process. All layers are laminated together under hydrostatic (or uni-axial) pressure at elevated temperature (500-600° C.) to evaporate the binder and solvent. Then the whole structure is sintered at 1370-1650° C., 30-50 hours, in a hydrogen atmosphere.

For small circuits, many modules are made on one substrate, and the individual circuits can be parted by breaking the substrate at the end of the process. Then the external contacts are brazed to the substrate, and finally gold may be plated on the surface with nickel as a diffusion barrier on top of the tungsten. The plating is preferably done electrolytically to achieve sufficient thickness and good conductivity if an electrical contact to all parts of the conductor pattern can be made. Otherwise, chemical plating is used.

During the process, the ceramic shrinks approximately 18% linearly. This is taken into consideration during the design of the circuit, both sideways and in thickness, which affects the characteristic impedance. As the shrinkage is material and process dependent, the finished circuits typically have linear dimensional tolerances 0.5-1%. These ceramic substrates have low TCE, a good thermal match to Si and GaAs as well as to leadless SMD components, good control over characteristic impedance, and good high frequency properties. Many layers are possible with high production yield because each layer can be inspected before the lamination, and faulty layers can be discarded. Among the disadvantages are low electrical conductivity in the inner layers (sheet resistivity~15 mohm/sq), and high dielectric constant, which gives delay, inferior pulse rise time and increased power loss and cross talk at very high frequencies.

The chemo/electro-active materials that contain more than one metal do not have to be a compound or solid solution, but can be a multi-phase physical mixture of discrete metals and/or metal oxides. As there will be varying degrees of solid state diffusion by the precursor materials from which the chemo/electro-active materials are formed, the final materials may exhibit composition gradients, and they can be crystalline or amorphous. Suitable metal oxides are those that i) when at a temperature of about 400° C. or above, have a resistivity of about 1 to about $10^6$ ohm-cm, preferably about 1 to about $10^5$ ohm-cm, and more preferably about 10 to about $10^4$ ohm-cm;

ii) show a chemo/electro response to at least one gas of interest; and iii) are stable and have mechanical integrity, that is are able to adhere to the substrate and not degrade at the operating temperature.

The metal oxides may also contain minor or trace amounts of hydration and elements present in the precursor materials.

The sensor materials may optionally contain one or more additives to promote adhesion to a substrate, or that alter the conductance, resistance or selectivity of the sensor material. Examples of additives to alter the conductance, resistance or selectivity of the sensor material include Ag, Au or Pt, as well as frits. Examples of additives to promote adhesion include frits, which are finely ground inorganic minerals that are transformed into glass or enamel on heating, or a rapidly quenched glass that retains its amorphous quality in the solid state. Frit precursor compounds are melted at high temperature and quenched, usually by rapidly pouring the melt into a fluid such as water, or by pouring through spinning metal rollers. The precursor compounds usually are a mechanical mixture of solid compounds such as oxides, nitrates or carbonates, or can be co-precipitated or gelled from a solution. Suitable precursor materials for frits include alkali and alkaline earth alumino-silicates and alumino-boro-silicates, copper, lead, phosphorus, titanium, zinc and zirconium. Frits as additives may be used in amounts of up to 30 volume percent, and preferably up to 10 volume percent, of the total volume of the chemo/electro-active material from which the sensor is made.

If desired, the sensor materials may also contain additives that, for example, catalyze the oxidation of a gas of interest or promote the selectivity for a particular analyte gas; or contain one or more dopants that convert an n semiconductor to a p semiconductor, or vice versa. These additives may be used in amounts of up to 30 weight percent, and preferably up to 10 weight percent, of the chemo/electro-active material from which the sensor is made.

Any frits or other additives used need not be uniformly or homogeneously distributed throughout the sensor material as fabricated, but may be localized on or near a particular surface thereof as desired. Each chemo/electro-active material may, if desired, be covered with a porous dielectric overlayer.

The chemo/electro-active materials used as sensor materials in this invention may, for example, be metal oxides of the formula $M^1O_x$, $M^1_aM^2_bO_x$, or $M^1_aM^2_bM^3_cO_x$; or mixtures thereof, wherein $M^1$, $M^2$ and $M^3$ are metals that form stable oxides when fired in the presence of oxygen above 500° C.;

$M^1$ is selected from Periodic Groups 2-15 and the lanthanide group;

$M^2$ and $M^3$ are each independently selected from Periodic Groups 1-15 and the lanthanide group;

$M^1$ and $M^2$ are not the same in $M^1{}_aM^2{}_bO_x$, and $M^1$, $M^2$ and $M^3$ are not the same in $M^1{}_aM^2{}_bM^3{}_cO_x$;

a, b, and c are each independently in the range of about 0.0005 to about 1; and x is a number sufficient so that the oxygen present balances the charges of the other elements present in the chemo/electro-active material.

In certain preferred embodiments, the metal oxide materials may include those in which $M^1$ is selected from the group consisting of Ce, Co, Cu, Fe, Ga, Nb, Ni, Pr, Ru, Sn, Ti, Tm, W, Yb, Zn, and Zr; and/or $M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr;

but in which $M^1$ and $M^2$ are not the same in $M^1{}_aM^2{}_bO_x$, and $M^1$, $M^2$ and $M^3$ are not the same in $M^1{}_aM^2{}_bM^3{}_cO_x$.

In certain other preferred embodiments, the metal oxide materials may include those in which $M^1O_x$ is $CeO_x$, $CoO_x$, $CuO_x$, $FeO_x$, $GaO_x$, $NbO_x$, $NiO_x$, $PrO_x$, $RuO_x$, $SnO_x$, $TaO_x$, $TiO_x$, $TmO_x$, $WO_x$, $YbO_x$, $ZnO_x$, $ZrO_x$, $SnO_x$ with Ag additive, $ZnO_x$ with Ag additive, $TiO_x$ with Pt additive, $ZnO_x$ with frit additive, $NiO_x$ with frit additive, $SnO_x$ with frit additive, or $WO_x$ with frit additive; and/or $M^1{}_aM^2{}_bO_x$ is $Al_aCr_bO_x$, $Al_aFe_bO_x$, $Al_aMg_bO_x$, $Al_aNi_bO_x$, $Al_aTi_bO_x$, $Al_aV_bO_x$, $Ba_aCu_bO_x$, $Ba_aSn_bO_x$, $Ba_aZn_bO_x$, $Bi_aRu_bO_x$, $Bi_aSn_bO_x$, $Bi_aZn_bO_x$, $Ca_aSn_bO_x$, $Ca_aZn_bO_x$, $Cd_aSn_bO_x$, $Cd_aZn_bO_x$, $Ce_aFe_bO_x$, $Ce_aNb_bO_x$, $Ce_aTi_bO_x$, $Ce_aV_bO_x$, $Co_aCu_bO_x$, $Co_aGe_bO_x$, $Co_aLa_bO_x$, $Co_aMg_bO_x$, $Co_aNb_bO_x$, $Co_aPb_bO_x$, $Co_aSn_bO_x$, $Co_aV_bO_x$, $Co_aW_bO_x$, $Co_aZn_bO_x$, $Cr_aCu_bO_x$, $Cr_aLa_bO_x$, $Cr_aMn_bO_x$, $Cr_aNi_bO_x$, $Cr_aSi_bO_x$, $Cr_aTi_bO_x$, $Cr_aY_bO_x$, $Cr_aZn_bO_x$, $Cu_aFe_bO_x$, $Cu_aGa_bO_x$, $Cu_aLa_bO_x$, $Cu_aNa_bO_x$, $Cu_aNi_bO_x$, $Cu_aPb_bO_x$, $Cu_aSn_bO_x$, $Cu_aSr_bO_x$, $Cu_aTi_bO_x$, $Cu_aZn_bO_x$, $Cu_aZr_bO_x$, $Fe_aGa_bO_x$, $Fe_aLa_bO_x$, $Fe_aMo_bO_x$, $Fe_aN_bO_x$, $Fe_aNi_bO_x$, $Fe_aSn_bO_x$, $Fe_aTi_bO_x$, $Fe_aW_bO_x$, $Fe_aZn_bO_x$, $Fe_aZr_bO_x$, $Ga_aLa_bO_x$, $Ga_aSn_bO_x$, $Ge_aNb_bO_x$, $Ge_aTi_bO_x$, $In_aSn_bO_x$, $K_aNb_bO_x$, $Mn_aNb_bO_x$, $Mn_aSn_bO_x$, $Mn_aTi_bO_x$, $Mn_aY_bO_x$, $Mn_aZn_bO_x$, $Mo_aPb_bO_x$, $Mo_aRb_bO_x$, $Mo_aSn_bO_x$, $Mo_aTi_bO_x$, $Mo_aZn_bO_x$, $Nb_aNi_bO_x$, $Nb_aNi_bO_x$, $Nb_aSr_bO_x$, $Nb_aTi_bO_x$, $Nb_aW_bO_x$, $Nb_aZr_bO_x$, $Ni_aSi_bO_x$, $Ni_aSn_bO_x$, $Ni_aY_bO_x$, $Ni_aZn_bO_x$, $Ni_aZr_bO_x$, $Pb_aSn_bO_x$, $Pb_aZn_bO_x$, $Rb_aW_bO_x$, $Ru_aSn_bO_x$, $Ru_aW_bO_x$, $Ru_aZn_bO_x$, $Sb_aSn_bO_x$, $Sb_aZn_bO_x$, $Sc_aZr_bO_x$, $Si_aSn_bO_x$, $Si_aTi_bO_x$, $Si_aW_bO_x$, $Si_aZn_bO_x$, $Sn_aTa_bO_x$, $Sn_aTi_bO_x$, $Sn_aW_bO_x$, $Sn_aZn_bO_x$, $Sn_aZr_bO_x$, $Sr_aTi_bO_x$, $Ta_aTi_bO_x$, $Ta_aZn_bO_x$, $Ta_aZr_bO_x$, $Ti_aV_bO_x$, $Ti_aW_bO_x$, $Ti_aZn_bO_x$, $Ti_aZr_bO_x$, $V_aZn_bO_x$, $V_aZr_bO_x$, $W_aZn_bO_x$, $W_aZr_bO_x$, $Y_aZr_bO_x$, $Zn_aZr_bO_x$, $Al_aNi_bO_x$ with frit additive, $Cr_aTi_bO_x$ with frit additive, $Fe_aLa_bO_x$ with frit additive, $Fe_aNi_bO_x$ with frit additive, $Fe_aTi_bO_x$ with frit additive, $Nb_aTi_bO_x$ with frit additive, $Nb_aW_bO_x$ with frit additive, $Ni_aZn_bO_x$ with frit additive, $Ni_aZr_bO_x$ with frit additive, $Sb_aSn_bO_x$ with frit additive, $Ta_aTi_bO_x$ with frit additive, or $Ti_aZn_bO_x$ with frit additive; and/or $M^1{}_aM^2{}_bM^3{}_cO_x$ is $Al_aMg_bZn_cO_x$, $Al_aSi_bV_cO_x$, $Ba_aCu_bTi_cO_x$, $Ca_aCe_bZr_cO_x$, $Co_aNi_bTi_cO_x$, $Co_aNi_bZr_cO_x$, $Co_aPb_bSn_cO_x$, $Co_aPb_bZn_cO_x$, $Cr_aSr_bTi_cO_x$, $Cu_aFe_bMn_cO_x$, $Cu_aLa_bSr_cO_x$, $Fe_aNb_bTi_cO_x$, $Fe_aPb_bZn_cO_x$, $Fe_aSr_bTi_cO_x$, $Fe_aTa_bTi_cO_x$, $Fe_aW_bZr_cO_x$, $Ga_aTi_bZn_cO_x$, $La_aMn_bNa_cO_x$, $La_aMn_bSr_cO_x$, $Mn_aSr_bTi_cO_x$, $Mo_aPb_bZn_cO_x$, $Nb_aSr_bTi_cO_x$, $Nb_aSr_bW_cO_x$, $Nb_aTi_bZn_cO_x$, $Ni_aSr_bTi_cO_x$, $Sn_aW_bZn_cO_x$, $Sr_aTi_bV_cO_x$, $Sr_aTi_bZn_cO_x$, or $Ti_aW_bZr_cO_x$.

In certain other preferred embodiments, the metal oxide materials may include those that are in an array of first and second chemo/electro-active materials, wherein the chemo/electro-active materials are selected from the pairings in the group consisting of (i) the first material is $M^1O_x$, and the second material is $M^1{}_aM^2{}_bO_x$;

(ii) the first material is $M^1O_x$, and the second material is $M^1{}_aM^2{}_bM^3{}_cO_x$;

(iii) the first material is $M^1{}_aM^2{}_bO_x$, and the second material is $M^1{}_aM^2{}_bM^3{}_cO_x$;

(iv) the first material is a first $M^1O_x$; and the second material is a second $M^1O_x$;

(v) the first material is a first $M^1{}_aM^2{}_bO_x$, and the second material is a second $M^1{}_aM^2{}_bO_x$; and (vi) the first material is a first $M^1{}_aM^2{}_bM^3{}_cO_x$, and the second material is a second $M^1{}_aM^2{}_bM^3{}_cO_x$;

wherein $M^1$ is selected from the group consisting of Ce, Co, Cu, Fe, Ga, Nb, Ni, Pr, Ru, Sn, Ti, Tm, W, Yb, Zn, and Zr;

$M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr;

but $M^1$ and $M^2$ are not the same in $M^1{}_aM^2{}_bO_x$, and $M^1$, $M^2$ and $M^3$ are not the same in $M^1{}_aM^2{}_bM^3{}_cO_x$;

a, b and c are each independently about 0.0005 to about 1; and x is a number sufficient so that the oxygen present balances the charges of the other elements present in the chemo/electro-active material.

In certain other preferred embodiments, an array of two or more chemo/electro-active materials may be selected from the group consisting of (i) the chemo/electro-active materials that include $M^1O_x$, (ii) the chemo/electro-active materials that include $M^1{}_aM^2{}_bO_x$, and (iii) the chemo/electro-active materials that include $M^1{}_aM^2{}_bM^3{}_cO_x$;

wherein $M^1$ is selected from the group consisting of Al, Ce, Cr, Cu, Fe, Ga, Mn, Nb, Ni, Pr, Sb, Sn, Ta, Ti, W and Zn;

wherein $M^2$ and $M^3$ are each independently selected from the group consisting of Ga, La, Mn, Ni, Sn, Sr, Ti, W, Y, Zn;

wherein $M^1$ and $M^2$ are each different in $M^1{}_aM^2{}_bO_x$, and $M^1$, $M^2$ and $M^3$ are each different in $M^1{}_aM^2{}_bM^3{}_cO_x$;

wherein a, b and c are each independently about 0.0005 to about 1; and wherein x is a number sufficient so that the oxygen present balances the charges of the other elements in the chemo/electro-active material.

$M^1$ may for example be selected from the group consisting of Al, Cr, Fe, Ga, Mn, Nb, Ni, Sb, Sn, Ta, Ti and Zn, or from the group consisting of Ga, Nb, Ni, Sb, Sn, Ta, Ti and Zn. $M^2$, $M^3$, or $M^2$ and $M^3$ may be selected from the group consisting of La, Ni, Sn, Ti and Zn, or the group consisting of Sn, Ti and Zn.

The array may contain other numbers of chemo/electro-active materials such as four or eight, and the array may contain at least one chemo/electro-active material that comprises M1Ox, and at least three chemo/electro-active materials that each comprise M1aM2bOx. Alternatively, the array may contain (i) at least one chemo/electro-active material that comprises M1Ox, and at least four chemo/electro-active materials that each comprise M1aM2bOx; or (ii) at least two chemo/electro-active materials that each comprise M1Ox, and at least four chemo/electro-active materials that each comprise M1aM2bOx; or (iii) at least three chemo/electro-active materials that each comprise M1aM2bOx, and at least one chemo/electro-active material that comprises M1aM2bM3cOx.

Chemo/electro-active materials useful in the apparatus of this invention may be selected from one or more members of the group consisting of a chemo/electro-active material that comprises $Al_aNi_bO_x$
a chemo/electro-active material that comprises $CeO_2$,
a chemo/electro-active material that comprises $Cr_aMn_bO_x$,
a chemo/electro-active material that comprises $Cr_aTi_bO_x$,
a chemo/electro-active material that comprises $Cr_aY_bO_x$
a chemo/electro-active material that comprises $Cu_aGa_bO_x$,
a chemo/electro-active material that comprises $Cu_aLa_bO_x$
a chemo/electro-active material that comprises CuO,
a chemo/electro-active material that comprises $Fe_aLa_bO_x$
a chemo/electro-active material that comprises $Fe_aNi_bO_x$
a chemo/electro-active material that comprises $Fe_aTi_bO_x$
a chemo/electro-active material that comprises $Ga_aTi_bZn_cO_x$
a chemo/electro-active material that comprises $Mn_aTi_bO_x$
a chemo/electro-active material that comprises $Nb_aSr_bO_x$,
a chemo/electro-active material that comprises $Nb_aTi_bO_x$
a chemo/electro-active material that comprises $Nb_aTi_bZn_cO_x$
a chemo/electro-active material that comprises $Nb_aW_bO_x$
a chemo/electro-active material that comprises NiO,
a chemo/electro-active material that comprises $Ni_aZn_bO_x$
a chemo/electro-active material that comprises $Pr_6O_{11}$,
a chemo/electro-active material that comprises $Sb_aSn_bO_x$.
a chemo/electro-active material that comprises $SnO_2$,
a chemo/electro-active material that comprises $Ta_aTi_bO_x$, and
a chemo/electro-active material that comprises $Ti_aZn_bO_x$.
a chemo/electro-active material that comprises $WO_3$, and
a chemo/electro-active material that comprises ZnO.
wherein a, b and c are each independently about 0.0005 to about 1; and wherein x is a number sufficient so that the oxygen present balances the charges of the other elements in the chemo/electro-active material.

Chemo/electro-active materials useful in this invention may also be selected from subgroups of the foregoing formed by omitting any one or more members from the whole group as set forth in the list above. As a result, the chemo/electro-active materials may in such instance not only be any one or more member(s) selected from any subgroup of any size that may be formed from the whole group as set forth in the list above, but the subgroup may also exclude the members that have been omitted from the whole group to form the subgroup. The subgroup formed by omitting various members from the whole group in the list above may, moreover, contain any number of the members of the whole group such that those members of the whole group that are excluded to form the subgroup are absent from the subgroup. Representative subgroups are set forth below.

Chemo/electro-active materials that comprise M1Ox may, for example, be selected from the group consisting of
a chemo/electro-active material that comprises $CeO_2$,
a chemo/electro-active material that comprises CuO,
a chemo/electro-active material that comprises NiO,
a chemo/electro-active material that comprises $Pr_6O_{11}$,
a chemo/electro-active material that comprises $SnO_2$,
a chemo/electro-active material that comprises $WO_3$, and
a chemo/electro-active material that comprises ZnO.
Of the above, one or more members of the group consisting of
a chemo/electro-active material that comprises $CeO_2$,
a chemo/electro-active material that comprises $SnO_2$, and
a chemo/electro-active material that comprises ZnO
may contain a frit additive.

A chemo/electro-active material that comprises M1aM2bOx, or a chemo/electro-active material that comprises M1aM2bM3cOx, may be selected from the group consisting of
a chemo/electro-active material that comprises $Al_aNi_bO_x$
a chemo/electro-active material that comprises $Cr_aMn_bO_x$,
a chemo/electro-active material that comprises $Cr_aTi_bO_x$
a chemo/electro-active material that comprises $Cr_aY_bO_x$
a chemo/electro-active material that comprises $Cu_aGa_bO_x$,
a chemo/electro-active material that comprises $Cu_aLa_bO_x$
a chemo/electro-active material that comprises $Fe_aLa_bO_x$
a chemo/electro-active material that comprises $Fe_aNi_bO_x$
a chemo/electro-active material that comprises $Fe_aTi_bO_x$
a chemo/electro-active material that comprises $Ga_aTi_bZn_cO_x$
a chemo/electro-active material that comprises $Mn_aTi_bO_x$
a chemo/electro-active material that comprises $Nb_aSr_bO_x$,
a chemo/electro-active material that comprises $Nb_aTi_bO_x$
a chemo/electro-active material that comprises $Nb_aTi_bZn_cO_x$
a chemo/electro-active material that comprises $Nb_aW_bO_x$
a chemo/electro-active material that comprises $Ni_aZn_bO_x$
a chemo/electro-active material that comprises $Sb_aSn_bO_x$.
a chemo/electro-active material that comprises $Ta_aTi_bO_x$, and
a chemo/electro-active material that comprises $Ti_aZn_bO_x$.
Of the above, one or more members of the group consisting of
a chemo/electro-active material that comprises $Al_aNi_bO_x$
a chemo/electro-active material that comprises $Cr_aTi_bO_x$
a chemo/electro-active material that comprises $Cu_aLa_bO_x$
a chemo/electro-active material that comprises $Fe_aLa_bO_x$
a chemo/electro-active material that comprises $Fe_aNi_bO_x$
a chemo/electro-active material that comprises $Fe_aTi_bO_x$
a chemo/electro-active material that comprises $Ga_aTi_bZn_cO_x$
a chemo/electro-active material that comprises $Nb_aTi_bO_x$
a chemo/electro-active material that comprises $Nb_aTi_bZn_cO_x$
a chemo/electro-active material that comprises $Nb_aW_bO_x$
a chemo/electro-active material that comprises $Ni_aZn_bO_x$
a chemo/electro-active material that comprises $Sb_aSn_bO_x$
a chemo/electro-active material that comprises $Ta_aTi_bO_x$, and
a chemo/electro-active material that comprises $Ti_aZn_bO_x$
may contain a frit additive.

In the apparatus of this invention, a chemo/electro-active material that comprises M1aM2bOx may be selected from the group consisting of
a chemo/electro-active material that comprises $Al_aNi_bO_x$
a chemo/electro-active material that comprises $Cr_aTi_bO_x$, and
a chemo/electro-active material that comprises $Fe_aLa_bO_x$.
or the group consisting of
a chemo/electro-active material that comprises $Cr_aTi_bO_x$
a chemo/electro-active material that comprises $Fe_aLa_bO_x$, and
a chemo/electro-active material that comprises $Fe_aNi_bO_x$
or the group consisting of
a chemo/electro-active material that comprises $Fe_aLa_bO_x$
a chemo/electro-active material that comprises $Fe_aNi_bO_x$, and
a chemo/electro-active material that comprises $Ni_aZn_bO_x$
or the group consisting of
a chemo/electro-active material that comprises $Fe_aNi_bO_x$
a chemo/electro-active material that comprises $Ni_aZn_bO_x$, and
a chemo/electro-active material that comprises $Sb_aSn_bO_x$.
or the group consisting of
a chemo/electro-active material that comprises $Al_aNi_bO_x$
a chemo/electro-active material that comprises $Cr_aTi_bO_x$ a chemo/electro-active material that comprises $Fe_aLa_bO_x$
a chemo/electro-active material that comprises $Fe_aNi_bO_x$
a chemo/electro-active material that comprises $Ni_aZn_bO_x$, and
a chemo/electro-active material that comprises $Sb_aSn_bO_x$.
or the group consisting of
a chemo/electro-active material that comprises $Al_aNi_bO_x$
a chemo/electro-active material that comprises $Cr_aTi_bO_x$, and
a chemo/electro-active material that comprises $Mn_aTi_bO_x$
or the group consisting of
a chemo/electro-active material that comprises $Nb_aTi_bO_x$
a chemo/electro-active material that comprises $Ni_aZn_bO_x$, and
a chemo/electro-active material that comprises $Sb_aSn_bO_x$
or the group consisting of
a chemo/electro-active material that comprises $Ni_aZn_bO_x$
a chemo/electro-active material that comprises $Sb_aSn_bO_x$, and
a chemo/electro-active material that comprises $Ta_aTi_bO_x$
or the group consisting of
a chemo/electro-active material that comprises $Sb_aSn_bO_x$
a chemo/electro-active material that comprises $Ta_aTi_bO_x$, and
a chemo/electro-active material that comprises $Ti_aZn_bO_x$.
or the group consisting of
a chemo/electro-active material that comprises $Cr_aMn_bO_x$
a chemo/electro-active material that comprises $Cr_aTi_bO_x$, and
a chemo/electro-active material that comprises $Cr_aY_bO_x$
or the group consisting of
a chemo/electro-active material that comprises $Cr_aTi_bO_x$
a chemo/electro-active material that comprises $Cr_aY_bO_x$, and
a chemo/electro-active material that comprises $Cu_aGa_bO_x$
or the group consisting of
a chemo/electro-active material that comprises $Cr_aY_bO_x$
a chemo/electro-active material that comprises $Cu_aGa_bO_x$, and
a chemo/electro-active material that comprises $Cu_aLa_bO_x$
or the group consisting of
a chemo/electro-active material that comprises $Cu_aGa_bO_x$
a chemo/electro-active material that comprises $Cu_aLa_bO_x$, and
a chemo/electro-active material that comprises $Fe_aLa_bO_x$.
or the group consisting of
a chemo/electro-active material that comprises $Cr_aMn_bO_x$
a chemo/electro-active material that comprises $Cr_aTi_bO_x$
a chemo/electro-active material that comprises $Cr_aY_bO_x$
a chemo/electro-active material that comprises $Cu_aGa_bO_x$
a chemo/electro-active material that comprises $Cu_aLa_bO_x$, and
a chemo/electro-active material that comprises $Fe_aLa_bO_x$.
or the group consisting of
a chemo/electro-active material that comprises $Cr_aY_bO_x$
a chemo/electro-active material that comprises $Cu_aGa_bO_x$, and
a chemo/electro-active material that comprises $Cu_aLa_bO_x$
or the group consisting of
a chemo/electro-active material that comprises $Cu_aGa_bO_x$,
a chemo/electro-active material that comprises $Cu_aLa_bO_x$, and
a chemo/electro-active material that comprises $Fe_aTi_bO_x$
or the group consisting of
a chemo/electro-active material that comprises $Cr_aMn_bO_x$
a chemo/electro-active material that comprises $Mn_aTi_bO_x$, and
a chemo/electro-active material that comprises $Nb_aSr_bO_x$ In the apparatus of this invention, a chemo/electro-active material that comprises M1aM2bOx, or a chemo/electro-active material that comprises M1aM2bM3cOx, may be selected from the group consisting of
a chemo/electro-active material that comprises $Cr_aTi_bO_x$
a chemo/electro-active material that comprises $Mn_aTi_bO_x$, and
a chemo/electro-active material that comprises $Nb_aTi_bZn_cO_x$
or the group consisting of
a chemo/electro-active material that comprises $Mn_aTi_bO_x$
a chemo/electro-active material that comprises $Nb_aTi_bZn_cO_x$, and
a chemo/electro-active material that comprises $Ta_aTi_bO_x$
or the group consisting of
a chemo/electro-active material that comprises $Nb_aTi_bZn_cO_x$
a chemo/electro-active material that comprises $Ta_aTi_bO_x$, and
a chemo/electro-active material that comprises $Ti_aZn_bO_x$.
or the group consisting of
a chemo/electro-active material that comprises $Al_aNi_bO_x$
a chemo/electro-active material that comprises $Cr_aTi_bO_x$
a chemo/electro-active material that comprises $Mn_aTi_bO_x$
a chemo/electro-active material that comprises $Nb_aTi_bZn_cO_x$
a chemo/electro-active material that comprises $Ta_aTi_bO_x$, and
a chemo/electro-active material that comprises $Ti_aZn_bO_x$.
or the group consisting of
a chemo/electro-active material that comprises $Ga_aTi_bZn_cO_x$
a chemo/electro-active material that comprises $Nb_aTi_bO_x$, and
a chemo/electro-active material that comprises $Ni_aZn_bO_x$
or the group consisting of
a chemo/electro-active material that comprises $Ga_aTi_bZn_cO_x$
a chemo/electro-active material that comprises $Nb_aTi_bO_x$
a chemo/electro-active material that comprises $Ni_aZn_bO_x$
a chemo/electro-active material that comprises $Sb_aSn_bO_x$
a chemo/electro-active material that comprises $Ta_aTi_bO_x$, and
a chemo/electro-active material that comprises $Ti_aZn_bO_x$.
or the group consisting of
a chemo/electro-active material that comprises $Cu_aLa_bO_x$
a chemo/electro-active material that comprises $Fe_aTi_bO_x$, and
a chemo/electro-active material that comprises $Ga_aTi_bZn_cO_x$
or the group consisting of
a chemo/electro-active material that comprises $Fe_aTi_bO_x$
a chemo/electro-active material that comprises $Ga_aTi_bZn_cO_x$, and
a chemo/electro-active material that comprises $Nb_aW_bO_x$.
or the group consisting of
a chemo/electro-active material that comprises $Cr_aY_bO_x$
a chemo/electro-active material that comprises $Cu_aGa_bO_x$
a chemo/electro-active material that comprises $Cu_aLa_bO_x$
a chemo/electro-active material that comprises $Fe_aTi_bO_x$
a chemo/electro-active material that comprises $Ga_aTi_bZn_cO_x$, and
a chemo/electro-active material that comprises $Nb_aW_bO_x$.

or the group consisting of
 a chemo/electro-active material that comprises $Mn_aTi_bO_x$
 a chemo/electro-active material that comprises $Nb_aSr_bO_x$, and
 a chemo/electro-active material that comprises $Nb_aTi_bZn_cO_x$ In the apparatus of this invention, a chemo/electro-active material that comprises M1Ox, a chemo/electro-active material that comprises M1aM2bOx, or a chemo/electro-active material that comprises M1aM2bM3cOx, may be selected from the group consisting of
 a chemo/electro-active material that comprises $Ga_aTi_bZn_cO_x$
 a chemo/electro-active material that comprises $Nb_aTi_bO_x$
 a chemo/electro-active material that comprises $Ni_aZn_bO_x$, and
 a chemo/electro-active material that comprises $SnO_2$
or the group consisting of
 a chemo/electro-active material that comprises $Ga_aTi_bZn_cO_x$
 a chemo/electro-active material that comprises $Nb_aTi_bO_x$
 a chemo/electro-active material that comprises $Ni_aZn_bO_x$
 a chemo/electro-active material that comprises $SnO_2$,
 a chemo/electro-active material that comprises $Ta_aTi_bO_x$, and
 a chemo/electro-active material that comprises $Ti_aZn_bO_x$.
or the group consisting of
 a chemo/electro-active material that comprises $Nb_aSr_bO_x$
 a chemo/electro-active material that comprises $Nb_aTi_bZn_cO_x$, and
 a chemo/electro-active material that comprises $Pr_6O_{11}$
or the group consisting of
 a chemo/electro-active material that comprises $Nb_aTi_bZn_cO_x$
 a chemo/electro-active material that comprises $Pr_6O_{11}$, and
 a chemo/electro-active material that comprises $Ti_aZn_bO_x$.
or the group consisting of
 a chemo/electro-active material that comprises $Cr_aMn_bO_x$
 a chemo/electro-active material that comprises $Mn_aTi_bO_x$
 a chemo/electro-active material that comprises $Nb_aSr_bO_x$
 a chemo/electro-active material that comprises $Nb_aTi_bZn_cO_x$
 a chemo/electro-active material that comprises $Pr_6O_{11}$, and
 a chemo/electro-active material that comprises $Ti_aZn_bO_x$.

In the apparatus of this invention, a chemo/electro-active material that comprises M1Ox, or a chemo/electro-active material that comprises M1aM2bOx may be selected from the group consisting of
 a chemo/electro-active material that comprises $Nb_aTi_bO_x$
 a chemo/electro-active material that comprises $Ni_aZn_bO_x$, and
 a chemo/electro-active material that comprises $SnO_2$.
or the group consisting of
 a chemo/electro-active material that comprises $Ni_aZn_bO_x$
 a chemo/electro-active material that comprises $SnO_2$, and
 a chemo/electro-active material that comprises $Ta_aTi_bO_x$
or the group consisting of
 a chemo/electro-active material that comprises $SnO_2$,
 a chemo/electro-active material that comprises $Ta_aTi_bO_x$, and
 a chemo/electro-active material that comprises $Ti_aZn_bO_x$.
or the group consisting of
 a chemo/electro-active material that comprises $Nb_aTi_bO_x$
 a chemo/electro-active material that comprises $Ni_aZn_bO_x$
 a chemo/electro-active material that comprises $Sb_aSn_bO_x$, and
 a chemo/electro-active material that comprises ZnO.
or the group consisting of
 a chemo/electro-active material that comprises $Ni_aZn_bO_x$
 a chemo/electro-active material that comprises $Sb_aSn_bO_x$
 a chemo/electro-active material that comprises $Ta_aTi_bO_x$, and
 a chemo/electro-active material that comprises ZnO
or the group consisting of
 a chemo/electro-active material that comprises $Sb_aSn_bO_x$
 a chemo/electro-active material that comprises $Ta_aTi_bO_x$
 a chemo/electro-active material that comprises $Ti_aZn_bO_x$, and
 a chemo/electro-active material that comprises ZnO
or the group consisting of
 a chemo/electro-active material that comprises $Ta_aTi_bO_x$
 a chemo/electro-active material that comprises $Ti_aZn_bO_x$, and
 a chemo/electro-active material that comprises ZnO.
or the group consisting of
 a chemo/electro-active material that comprises $Nb_aTi_bO_x$
 a chemo/electro-active material that comprises $Ni_aZn_bO_x$
 a chemo/electro-active material that comprises $Sb_aSn_bO_x$
 a chemo/electro-active material that comprises $Ta_aTi_bO_x$
 a chemo/electro-active material that comprises $Ti_aZn_bO_x$, and
 a chemo/electro-active material that comprises ZnO.
or the group consisting of
 a chemo/electro-active material that comprises $Al_aNi_bO_x$
 a chemo/electro-active material that comprises $Cr_aMn_bO_x$, and
 a chemo/electro-active material that comprises CuO
or the group consisting of
 a chemo/electro-active material that comprises $Cr_aMn_bO_x$
 a chemo/electro-active material that comprises CuO, and
 a chemo/electro-active material that comprises $Nb_aSr_bO_x$
or group consisting of
 a chemo/electro-active material that comprises CuO
 a chemo/electro-active material that comprises $Nb_aSr_bO_x$, and
 a chemo/electro-active material that comprises $Pr_6O_{11}$
or group consisting of
 a chemo/electro-active material that comprises $Nb_aSr_bO_x$
 a chemo/electro-active material that comprises $Pr_6O_{11}$, and
 a chemo/electro-active material that comprises $WO_3$.
or group consisting of
 a chemo/electro-active material that comprises $Al_aNi_bO_x$
 a chemo/electro-active material that comprises $Cr_aMn_bO_x$
 a chemo/electro-active material that comprises CuO
 a chemo/electro-active material that comprises $Nb_aSr_bO_x$
 a chemo/electro-active material that comprises $Pr_6O_{11}$, and
 a chemo/electro-active material that comprises $WO_3$.

Any method of depositing the chemo/electro-active material to a substrate is suitable. One technique used for deposition is applying a semiconducting material on an alumina substrate on which electrodes are screen printed. The semiconducting material can be deposited on top of electrodes by hand painting semiconducting materials onto the substrate, pipetting materials into wells, thin film deposition, or thick film printing techniques. Most techniques are followed by a final firing to sinter the semiconducting materials.

Figure 2:
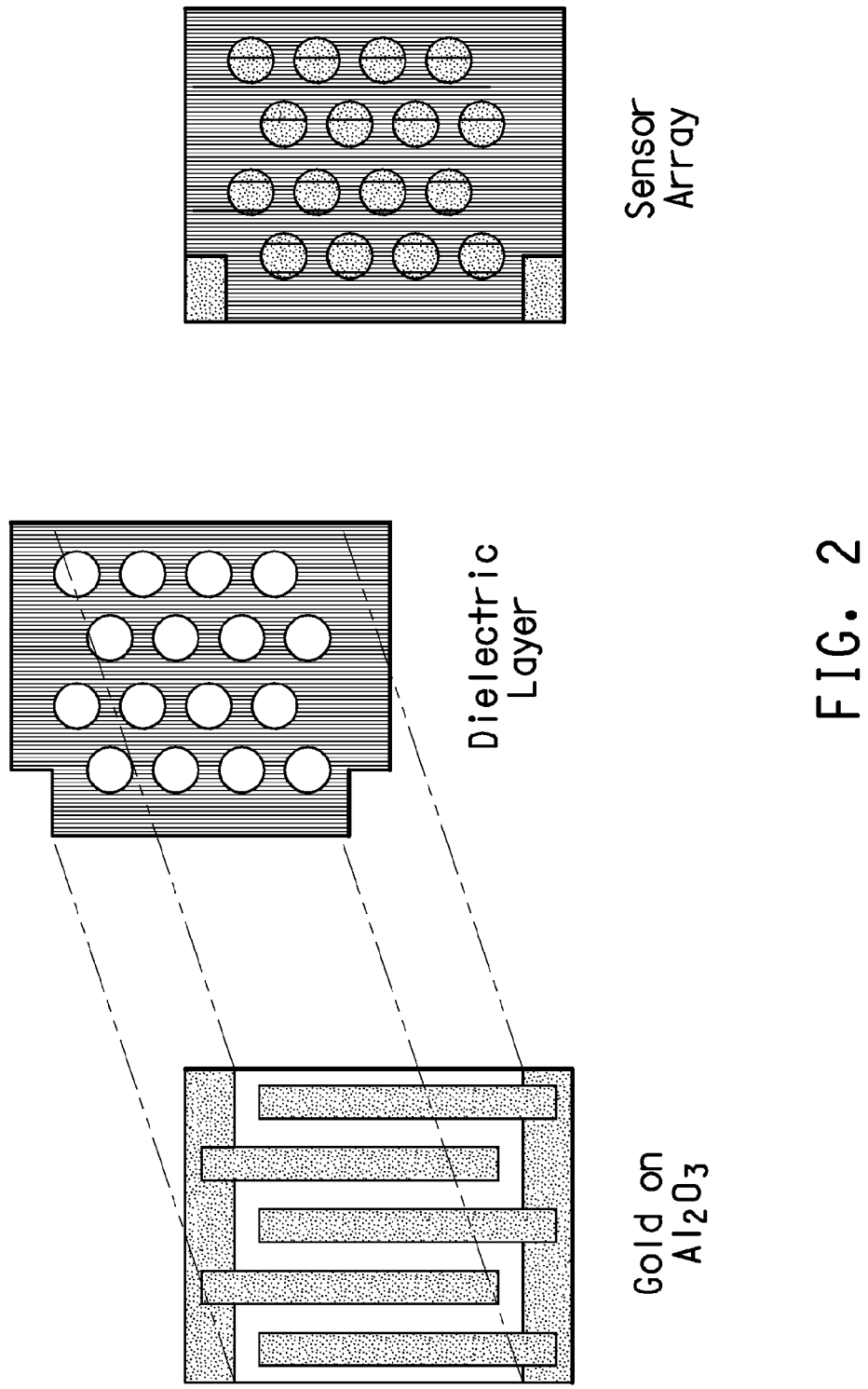
FIG. 2 is a schematic of the pattern of interdigitated electrodes overlaid with a dielectric overlayer, forming sixteen blank wells, in an array of chemo/electro-active materials.
Figure 3A:
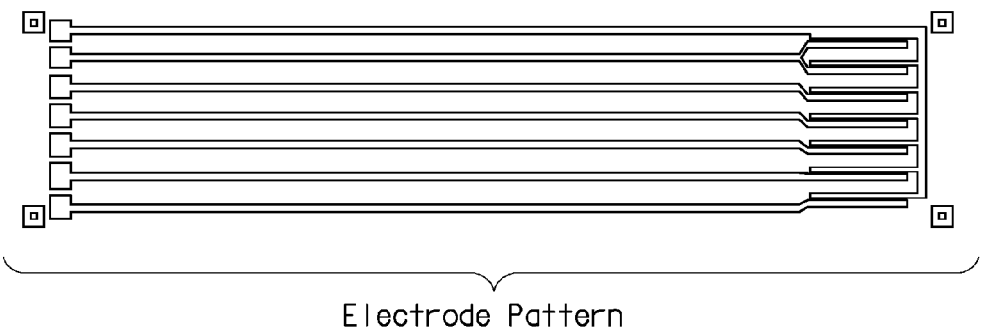
FIG. 3 depicts the electrode pattern, dielectric pattern, and sensor material pattern in an array of chemo/electro-active materials.
Figure 3B:
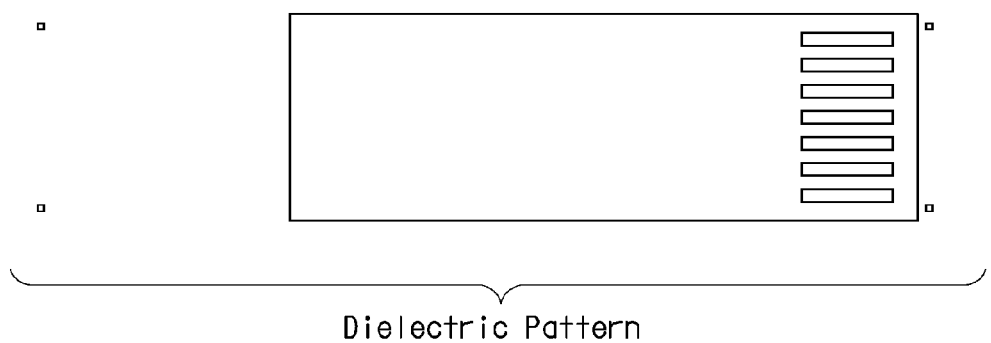
Figure 3C:
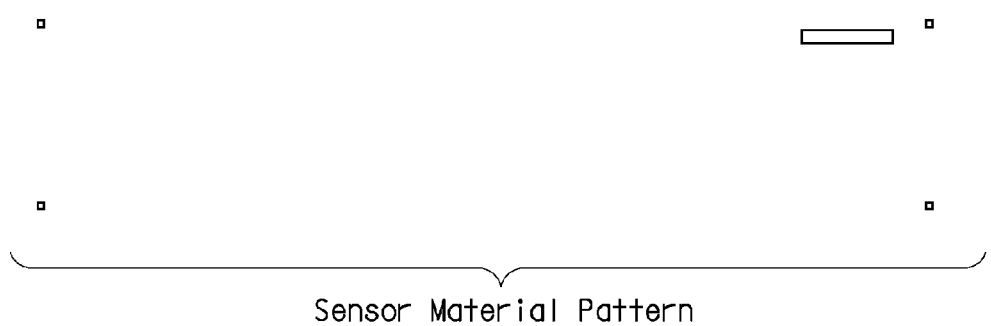

Techniques for screen-printing substrates with the electrodes and chemo/electro-active materials are illustrated in FIGS. 2-3. FIG. 2 depicts a method of using interdigitated electrodes overlaid with dielectric material, forming blank wells into which the chemo/electro-active materials can be deposited. FIG. 3 depicts an electrode screen pattern for an array of 6 materials which is printed on both sides of the substrate to provide for a 12-material array chip. Two of the electrodes are in parallel so it holds only 6 unique materials. Counting down from the top of the array shown in FIG. 3, the top two materials can only be accessed simultaneously by the split electrode with which they have shared contact. Below that is the screen pattern for the dielectric material, which is screen printed on top of the electrodes on both sides of the substrate to prevent the material from being fouled by contact with the gas mixture, such as a deposit of soot that could reduce the sensitivity of a sensor material to a gas or cause a short. Below that is the screen pattern for the actual sensor materials. This is printed in the holes in the dielectric on top of the electrodes. When more than one material is used in the array, the individual materials are printed one at a time.

The geometry of a sensor material as fabricated in an array, including such characteristics as its thickness, selection of a compound or composition for use as the sensor, and the voltage applied across the array, can vary depending on the sensitivity required. If desired, the apparatus may be constructed in a size such that it may be passed through an opening that is the size of a circle having a diameter of no more than about 150 mm, or no more than about 100 mm, or no more than about 50 mm, or no more than about 25 mm, or no more than about 18 mm, as the requirements of it usage may dictate. The sensor materials are preferably connected in parallel in a circuit to which a voltage of about 1 to about 20, preferably about 1 to about 12, volts is applied across the sensor materials.

As noted, the types of electrical response characteristics that may be measured include AC impedance or resistance, capacitance, voltage, current or DC resistance. It is preferred to use resistance as the electric response characteristic of a sensor material that is measured to perform analysis of a gas mixture and/or a component therein. For example, a suitable sensor material may be that which, when at a temperature of about 400° C. or above, has a resistivity of at least about 1 ohm-cm, and preferably at least about 10 ohm-cm, and yet no more than about $10^6$ ohm-cm, preferably no more than about $10^5$ ohm-cm, and more preferably no more than about $10^4$ ohm-cm. Such a sensor material may also be characterized as that which exhibits, preferably at a temperature of about 400° C. or above, upon exposure to a gas mixture, a change in resistance of at least about 0.1 percent, and preferably at least about 1 percent, as compared to the resistance in the absence of exposure. Using such material, a signal may be generated that is proportional to the resistance of exhibited by the material when it is exposed to a multi-component gas mixture.

Regardless of the type of response characteristic that is measured for the purpose of analyzing a mixture and/or a gaseous component of interest therein, it is desirable that a sensor material be utilized for which a quantified value of that response characteristic is stable over an extended period of time. When the sensor material is exposed to a mixture containing the analyte, the concentration of the analyte being a function of the composition of the particular gas mixture in which it is contained, the value of the response of the sensor material will preferably remain constant or vary to only a small extent during exposure to the mixture over an extended period of time at a constant temperature. For example, the value of the response, if it varies, will vary by no more than about twenty percent, preferably no more than about ten percent, more preferably no more than about five percent, and most preferably no more than about one percent over a period of at least about 1 minute, or preferably a period of hours such as at least about 1 hour, preferably at least about 10 hours, more preferably at least about 100 hours, and most preferably at least about 1000 hours. One of the advantages of the types of sensor materials described above is that they are characterized by this kind of stability of response.

The electrical response characteristic exhibited by a chemo/electro-active material in respect of a multi-component gas mixture that contains an analyte gas or sub-group of gases derives from contact of the surface of the chemo/electro-active material with the gas mixture containing the analyte(s). The electrical response characteristic is an electrical property, such as capacitance, voltage, current, AC impedance, or AC or DC resistance, that is affected by exposure of the chemo/electro-active material to the multi-component gas mixture. A quantified value of, or a signal proportional to the quantified value of, the electrical property or a change in the electrical property may be obtained as a useful measurement at one or more times while the material is exposed to the gas mixture.

An electrical response is determined for each chemo/electro-active material upon exposure of the array to a gas mixture, and means for determining the response include conductors interconnecting the sensor materials. The conductors are in turn connected to electrical input and output circuitry, including data acquisition and manipulation devices as appropriate to measure and record a response exhibited by a sensor material in the form of an electrical signal. The value of a response, such as a measurement related to resistance, may be indicated by the size of the signal. One or more signals may be generated by an array of sensors as to each analyte component in the mixture, whether the analyte is one or more individual gases and/or one or more subgroups of gases.

An electrical response is determined for each individual chemo/electro-active material separately from that of each of the other chemo/electro-active materials. This can be accomplished by accessing each chemo/electro-active material with an electric current sequentially, using a multiplexer to provide signals differentiated between one material and another in, for example, the time domain or frequency domain. It is consequently preferred that no chemo/electro-active material be joined in a series circuit with any other such material. One electrode, by which a current is passed to a chemo/electro-active material, can nevertheless be laid out to have contact with more than one material. An electrode may have contact with all, or fewer than all, of the chemo/electro-active materials in an array. For example, if an array has 12 chemo/electro-active materials, an electrode may have contact with each member of a group of 2, 3, 4, 5 or 6 (or, optionally, more in each instance) of the chemo/electro-active materials. The electrode will preferably be laid out to permit an electrical current to be passed to each member of such group of chemo/electro-active materials sequentially.

A conductor such as a printed circuit may be used to connect a voltage source to a sensor material, and, when a voltage is applied across the sensor material, a corresponding current is created through the material. Although the voltage may be AC or DC, the magnitude of the voltage will typically be held constant. The resulting current is proportional to both the applied voltage and the resistance of the sensor material. A response of the material in the form of either the current, voltage or resistance may be determined, and means for doing so include commercial analog circuit components such as precision resistors, filtering capacitors and operational amplifiers (such as a OPA4340). As voltage, current and resistance is each a known function of the other two electrical properties, a known quantity for one property may be readily converted to that of another.

Resistance may be determined, for example, in connection with the digitization of an electrical response. Means for digitizing an electrical response include an analog to digital (A/D) converter, as known in the art, and may include, for example, electrical components and circuitry that involve the operation of a comparator. An electrical response in the form of a voltage signal, derived as described above as a result of applying a voltage across a sensor material, is used as an input to a comparator section (such as a LM339). The other input to the comparator is driven by a linear ramp produced by charging a capacitor using a constant current source configured from an operational amplifier (such as a LT1014) and an external transistor (such as a PN2007a). The ramp is controlled and monitored by a microcomputer (such as a T89C51CC01). A second comparator section is also driven by the ramp voltage, but is compared to a precise reference voltage. The microcomputer captures the length of time from the start of the ramp to the activation of the comparators to generate a signal based on the counted time.

The resistance of the sensor material is then calculated, or quantified as a value, by the microcomputer from the ratio of the time signal derived from the voltage output of the material to a time signal corresponding to a known look-up voltage and, ultimately, to the resistance that is a function of the look-up voltage. A microprocessor chip, such as a T89C51CC01, can be used for this function. The microprocessor chip may also serve as means for determining a change in the resistance of a sensor material by comparing a resistance, determined as above, to a previously determined value of the resistance.

Electrical properties such as impedance or capacitance may be determined, for example, by the use of circuitry components such as an impedance meter, a capacitance meter or inductance meter.

Means for digitizing the temperature of an array of chemo/electro-active materials can include, for example, components as described above that convert a signal representative of a physical property, state or condition of a temperature-measuring device to a signal based on counted time.

In one embodiment, analysis of a multi-component gas mixture is complete upon the generation of an electrical response, such as resistance, in the manner described above. As a measurement of resistance exhibited by a sensor material upon exposure to a gas mixture is a function of the partial pressure within the mixture of one or more component gases, the measured resistance provides useful information about the composition of the gas mixture. The information may, for example, indicate the presence or absence within the mixture of a particular gas or subgroup of gases. In other embodiments, however, it may be preferred to manipulate, or further manipulate, an electrical response in the manner necessary to obtain information related to the concentration within the mixture of one or more particular component gases or subgroups of gases, or to calculate the actual concentration within the mixture of one or more component gases or subgroups.

Means for obtaining information concerning the relative concentration within the mixture of one or more individual component gases and/or one or more subgroups of gases, or for detecting the presence of, or calculating the actual concentration of, one or more individual component gases and/or subgroups within the mixture, may include a modeling algorithm that incorporates either a PLS (Projection onto Latent Systems) model, a back-propagation neural network model, or a combination of the two, along with signal pre-processing and output post-processing. Signal pre-processing includes, but is not limited to, such operations as principle component analyses, simple linear transformations and scaling, logarithmic and natural logarithmic transformations, differences of raw signal values (e.g., resistances), and differences of logarithmic values. The algorithm contains a model whose parameters have been previously determined, and that empirically models the relationship between the pre-processed input signal and information related to the gas concentration of the species of interest. Output post-processing includes, but is not limited to, all of the operations listed above, as well as their inverse operations.

The model is constructed using equations in which constants, coefficients or other factors are derived from pre-determined values characteristic of a precisely measured electrical response of an individual sensor material to a particular individual gas or subgroup expected to be present as a component in the mixture to be analyzed. The equations may be constructed in any manner that takes temperature into account as a value separate and apart from the electrical responses exhibited by the sensor materials upon exposure to a gas mixture. Each individual sensor material in the array differs from each of the other sensors in its response to at least one of the component gases or subgroups in the mixture, and these different responses of each of the sensors is determined and used to construct the equations used in the model.

A change of temperature in the array may be indicated by a change in the quantified value of an electrical response characteristic, resistance for example, of a sensor material. At a constant partial pressure in the mixture of a gas of interest, the value of an electrical response characteristic of a sensor material may vary with a change in temperature of the array, and thus the material. This change in the value of an electrical response characteristic may be measured for the purpose of determining or measuring the extent of change of, and thus a value for, temperature. The temperature of the array will be the same, or substantially the same, as the temperature of the gas mixture unless the array is being maintained at a preselected temperature by a heater located on the substrate. If the array is being heated by a heater, the temperature of the array will lie substantially in the range within which the heater cycles on and off.

It is not required, but is preferred, that the measurement of temperature be made independently of information related to the compositional content of a gas mixture. This can be done by not using sensors that provide compositional information for the additional purpose of determining temperature, and, optionally, by connecting the temperature measuring device in parallel circuitry with the sensor materials, rather than in series. Means for measuring temperature include a thermocouple or a pyrometer incorporated with an array of sensors. If the temperature determining device is a thermistor, which is typically a material that is not responsive to an analyte gas, the thermistor is preferably made from a different material than the material from which any of the gas sensors is made. Regardless of the method by which temperature or change in temperature is determined, a temperature value or a quantified change in temperature is a desirable input, preferably in digitized form, from which an analysis of a mixture of gases and/or a component therein may be performed.

In the method and apparatus of this invention, unlike various prior-art technologies, there is no need to separate the component gases of a mixture for purposes of performing an analysis, such as by a membrane or electrolytic cell. There is also no need when performing an analysis by means of this invention to employ a reference gas external to the system, such as for the purpose of bringing a response or analytical results back to a base line value. A value representative of a reference state may, however, be used as a factor in an algorithm by which information related to the composition of the gas mixture is determined. With the exception of preliminary testing, during which a standardized response value to be assigned to the exposure of each individual sensor material to each individual analyte gas is determined, the sensor materials are exposed only to the mixture in which an analyte gas and/or subgroup is contained. The sensor materials are not exposed to any other gas to obtain response values for comparison to those obtained from exposure to the mixture containing an analyte. The analysis of the mixture is therefore performed only from the electrical responses obtained upon exposure of the chemo/electro-active materials to the mixture containing the analyte. No information about an analyte gas and/or subgroup is inferred by exposure of the sensor materials to any gas other than the analyte itself as contained within the mixture.

This invention is therefore useful at the higher temperatures found in automotive emission systems, typically in the range of from about 400° C. to about 1000° C. In addition to gasoline and diesel internal combustion engines, however, there is a variety of other combustion processes to which this invention could be applied, including stack or burner emissions of all kinds such as resulting from chemical manufacturing, electrical generation, waste incineration and air heating. These applications require the detection of gases such as nitrogen oxides, ammonia, carbon monoxide, hydrocarbons and oxygen at the ppm to per cent levels, typically in a highly corrosive environment.

When the multi-component gas mixture comprises a nitrogen oxide, a hydrocarbon, or both, or any of the other gases mentioned herein, the apparatus may be used to determine the presence and/or concentration of a nitrogen oxide and/or hydrocarbon in the multi-component gas mixture. The apparatus may also be used to determine the presence and/or concentration of any one or more to the other gases mentioned herein that may be present in a multi-component gas mixture. For this purpose, the electrical response, in the apparatus of this invention, of one or more of a chemo/electro-active material that comprises $M^1O_x$, a chemo/electro-active material that comprises $M^1_aM^2_bO_x$, and a chemo/electro-active material that comprises $M^1_aM^2_bM^3_cO_x$, may be related to one or more of the presence of a nitrogen oxide within the gas mixture, the presence of a hydrocarbon within the gas mixture, the collective concentration of all nitrogen oxides within the gas mixture, and the concentration of a hydrocarbon within the gas mixture.

This invention therefore provides methods and apparatus for directly sensing the presence and/or concentration of one or more gases in an multi-component gas system, comprising an array of at least two chemo/electro-active materials chosen to detect analyte gases or subgroups of gases in a multi-component gas stream. The multi-component gas system can be at essentially any temperature that is not so low or so high that the sensor materials are degraded or the sensor apparatus otherwise malfunctions. In one embodiment, the gas system may be at a lower temperature such as room temperature (about 25° C.) or elsewhere in the range of about 0° C. to less than about 100° C., whereas in other embodiments the gas mixture may at a higher temperature such as in the range of about 400° C. to about 1000° C. or more. The gas mixture may therefore have a temperature that is about 0° C. or more, about 100° C. or more, about 200° C. or more, about 300° C. or more, about 400° C. or more, about 500° C. or more, about 600° C. or more, about 700° C. or more, or about 800° C. or more, and yet is less than about 1000° C., is less than about 900° C., is less than about 800° C., is less than about 700° C., is less than about 600° C., is less than about 500° C., is less than about 400° C., is less than about 300° C., is less than about 200° C., or is less than about 100° C.

In applications in which the gas mixture is above about 400° C., the temperature of the sensor materials and the array may be determined substantially only, and preferably is determined solely, by the temperature of the gas mixture in which a gaseous analyst is contained. This is typically a variable temperature. When higher-temperature gases are being analyzed, it may be desirable to provide a heater with the array to bring the sensor materials quickly to a minimum temperature. Once the analysis has begun, however, the heater (if used) is typically switched off, and no method is provided to maintain the sensor materials at a preselected temperature. The temperature of the sensor materials thus rises or falls to the same extent that the temperature of the surrounding environment does. The temperature of the surrounding environment, and thus the sensors and the array, is typically determined by (or results from) substantially only the temperature of the gas mixture to which the array is exposed.

In applications in which the gas mixture is below about 400° C., it may be preferred to maintain the sensor materials and the array at a preselected temperature of about 200° C. or above, and preferably 400° C. or above. This preselected temperature may be substantially constant, or preferably is constant. The preselected temperature may also be about 500° C. or above, about 600° C. or above, about 700° C. or above, about 800° C. or above, about 900° C. or above, or about 1000° C. or above. This may be conveniently done with a heater incorporated with the array, in a manner as known in the art. If desired, a separate micro heater means may be supplied for each separate chemo/electro-active material, and any one or more of the materials may be heated to the same or a different temperature. The temperature of the gas mixture in such case may also be below about 300° C., below about 200° C., below about 100° C., or below about 50° C. In these low temperature application, the means for heating the chemo/electro-active materials may be a voltage source that has a voltage in the range of about $10^{-3}$ to about $10^{-6}$ volts. The substrate on which the materials are placed may be made of a materials that is selected from one or more of the group consisting of silicon, silicon carbide, silicon nitride, and alumina containing a resistive dopant. Devices used in these low temperature applications are often small enough to be held in the human hand.

This heating technique is also applicable, however, to the analysis of high temperature gases. When the temperature of the gas mixture is above about 400° C., the sensor materials may nevertheless be maintained by a heater at a constant or substantially constant preselected temperature that is higher than the temperature of the gas mixture. Such preselected temperature may be about 500° C. or above, about 600° C. or above, about 700° C. or above, about 800° C. or above, about 900° C. or above, or about 1000° C. or above. Should the temperature of the gas mixture exceed the temperature preselected for the heater, the heater may be switched off during such time. A temperature sensor will still be employed, however, to measure the temperature of the gas mixture and provide that value as an input to an algorithm by which information related to the composition of the gas mixture is determined.

In summary, it may be seen that this invention provides means to determine, measure and record responses exhibited by each of the chemo/electro-active materials present in an array upon exposure to a gas mixture. Any means that will determine, measure and record changes in electrical properties can be used, such as a device that is capable of measuring the change in AC impedance of the materials in response to the concentration of adsorbed gas molecules at their surfaces. Other means for determining electrical properties are suitable devices to measure, for example, capacitance, voltage, current or DC resistance. Alternatively a change in temperature of the sensing material may be measured and recorded. The chemical sensing method and apparatus may further provide means to measure or analyze a mixture and/or the detected gases such that the presence of the gases are identified and/or their concentrations are measured. These means can include instrumentation or equipment that is capable, for example, of performing chemometrics, neural networks or other pattern recognition techniques. The chemical sensor apparatus will further comprise a housing for the array of chemo/electro-active materials, the means for detecting, and means for analyzing.

The device includes a substrate, an array of at least two chemo/electro-active materials chosen to detect one or more predetermined gases in a multi-component gas stream, and a means to detect changes in electrical properties in each of the chemo/electro-active materials present upon exposure to the gas system. The array of sensor materials should be able to detect an analyte of interest despite competing reactions caused by the presence of the several other components of a multi-component mixture. For this purpose, this invention uses an array or multiplicity of sensor materials, as described herein, each of which has a different sensitivity for at least one of the gas components of the mixture to be detected. A sensor that has the needed sensitivity, and that can operate to generate the types of analytical measurements and results described above, is obtained by selection of appropriate compositions of materials from which the sensor is made. Various suitable types of materials for this purpose are described above. The number of sensors in the array is typically greater than or equal to the number of individual gas components to be analyzed in the mixture.

Further description relevant to the apparatus of this invention, uses for the apparatus and methods of using the apparatus may be found in U.S. Provisional Application No. 60/370,445, filed Apr. 5, 2002, and U.S. application Ser. No. 10/117,472, filed Apr. 5, 2002, each of which is incorporated in its entirety as a part hereof for all purposes.

What is claimed is:

1. An apparatus for reducing a nitrogen oxide gas emitted by a emissions source, comprising
    (a) an emissions source,
    (b) an exhaust conduit for transporting the nitrogen oxide gas downstream from the emissions source,
    (c) an injector for injecting a reducing agent into the conduit, and
    (d) one or more gas analyzers located in the conduit upstream from the injector,
    wherein a gas analyzer comprises an array of chemo/electro-active materials selected as a member from the group of five arrays of chemo/electro-active material consisting of:
    (i) an array comprising $SnO_x$, $Nb_aTi_bO_x$, and $Ni_aZn_bO_x$;
    (ii) an array comprising $ZnO_x$, $Ti_aZn_bO_x$, and $Ta_aTi_bO_x$;
    (iii) an array comprising $Sb_aSn_bO_x$, $Ta_aTi_bO_x$, and $Ti_aZn_bO_x$;
    (iv) an array comprising $SnO_x$, $Ta_aTi_bO_x$, and $Ti_aZn_bO_x$; and
    (v) an array comprising $Ni_aZn_bO_x$, $SnO_x$, and $Ta_aTi_bO_x$;
    wherein a, b and c are each independently about 0.0005 to about 1; and
    wherein x is a number sufficient so that the oxygen present balances the charges of the other elements in the chemo/electro-active material.

2. An apparatus according to claim 1 further comprising a catalyst to catalyze the reduction of the nitrogen oxide.

3. An apparatus according to claim 2 further comprising a gas analyzer that is downstream from the injector and downstream from a catalyst.

4. An apparatus according to claim 2 wherein a first gas analyzer is located upstream from a catalyst, and a second gas analyzer is located downstream from the catalyst.

5. An apparatus according to claim 2 that comprises a plurality of gas analyzers, wherein a plurality of gas analyzers is located upstream from a catalyst, and a plurality of gas analyzers is located downstream from the catalyst.

6. An apparatus according to claim 2 comprising (a) a first catalyst, (b) a gas analyzer located downstream from the first catalyst, and (c) a second catalyst located downstream from the gas analyzer.

7. An apparatus according to claim 6 wherein the first and second catalysts is each a catalyst bed in vertical arrangement.

8. An apparatus according to claim 6 further comprising a plurality of gas analyzers located between the first and second catalysts.

9. An apparatus according to claim 6 further comprising one or more gas analyzers downstream from the second catalyst.

10. An apparatus according to claim 2 further comprising one or more gas analyzers downstream from all catalysts.

11. An apparatus according to claim 1 or 2 wherein the reducing agent is ammonia.

12. An apparatus according to claim 1 or 2 wherein the reducing agent is urea.

13. An apparatus according to claim 1 or 2 wherein the emissions source is stationary.

* * * * *